United States Patent
d'Esterre et al.

(10) Patent No.: US 11,883,222 B2
(45) Date of Patent: Jan. 30, 2024

(54) SYSTEM AND METHOD FOR GENERATING PERFUSION FUNCTIONAL MAPS FROM TEMPORALLY RESOLVED HELICAL COMPUTED TOMOGRAPHIC IMAGES

(71) Applicant: Andromeda Medical Imaging Inc., Calgary (CA)

(72) Inventors: Christopher d'Esterre, Calgary (CA); Connor McDougall, Calgary (CA); Philip Barber, Calgary (CA)

(73) Assignee: Andromeda Medical Imaging Inc., Calgary (CA)

( * ) Notice: Subject to any disclaimer, the term of this patent is extended or adjusted under 35 U.S.C. 154(b) by 357 days.

(21) Appl. No.: 17/426,624

(22) PCT Filed: Jan. 29, 2020

(86) PCT No.: PCT/CA2020/050108
§ 371 (c)(1),
(2) Date: Jul. 28, 2021

(87) PCT Pub. No.: WO2020/154807
PCT Pub. Date: Aug. 6, 2020

(65) Prior Publication Data
US 2022/0087631 A1 Mar. 24, 2022

Related U.S. Application Data

(60) Provisional application No. 62/798,358, filed on Jan. 29, 2019.

(51) Int. Cl.
*A61B 6/00* (2006.01)
*G06T 7/38* (2017.01)
(Continued)

(52) U.S. Cl.
CPC .............. *A61B 6/507* (2013.01); *A61B 6/027* (2013.01); *A61B 6/032* (2013.01); *A61B 6/504* (2013.01);
(Continued)

(58) Field of Classification Search
None
See application file for complete search history.

(56) References Cited

U.S. PATENT DOCUMENTS 6,650,928 B1 11/2003 Gailly et al.
6,898,453 B2 5/2005 Lee
(Continued)

FOREIGN PATENT DOCUMENTS

WO 2008034182 A1 3/2008

OTHER PUBLICATIONS

Time-Dependent Computed Tomographic Perfusion Thresholds for Patients With Acute Ischemic Stroke, by D'Esterre et al., stroke 46.12 (2015): 3390-3397 (Year: 2015).*
(Continued)

*Primary Examiner* — Vikkram Bali
(74) *Attorney, Agent, or Firm* — BERESKIN & PARR LLP/S.E.N.C.R.L. s.r.l; Tonino Rosario Orsi

(57) ABSTRACT

Various methods and systems are described for obtaining at least one CTA perfusion functional map from Time Resolved Helical CTA (TRH-CTA) image data. At least one processor may be configured to preprocess the TRH-CTA helical image data to generate preprocessed TRH-CTA helical image data; generate time density curve data for a plurality of voxels from the preprocessed TRH-CTA helical image data for an axial imaging slice, where the time density curve data comprise intensity values for different phases of the preprocessed TRH-CTA helical image data arranged sequentially in time; generate at least one perfusion func-
(Continued)

tional map for the axial imaging slice by at least one of: (1) applying at least one mapping function to different phases of the time density curve data corresponding to the axial imaging slice; (2) applying a deconvolution method to the time density curve data; and (3) applying a non-deconvolution method to the time density curve data; and perform spatial filtering on the perfusion functional map. A display may be used to display at least one filtered perfusion functional map.

20 Claims, 13 Drawing Sheets

(51) Int. Cl.
*A61B 6/02* (2006.01)
*A61B 6/03* (2006.01)
*G06T 11/00* (2006.01)

(52) U.S. Cl.
CPC .............. *A61B 6/5205* (2013.01); *G06T 7/38* (2017.01); *G06T 11/003* (2013.01); *G06T 11/008* (2013.01); *G06T 2207/10081* (2013.01); *G06T 2207/20081* (2013.01); *G06T 2207/30016* (2013.01); *G06T 2207/30104* (2013.01)

(56) References Cited

U.S. PATENT DOCUMENTS

| | | | |
|---|---|---|---|
| 9,324,143 | B2 | 4/2016 | Goyal |
| 9,486,176 | B2 | 11/2016 | Goyal |
| 10,045,755 | B2 | 8/2018 | Meetz et al. |
| 2004/0218794 | A1 | 11/2004 | Kao et al. |
| 2005/0018808 | A1* | 1/2005 | Piacsek .................. A61B 6/481 378/5 |
| 2011/0211742 | A1 | 9/2011 | Bredno et al. |

OTHER PUBLICATIONS

Perfusion Computed Tomography for the Evaluation of Acute Ischemic Stroke, Strengths and Pitfalls, by Heit et al., Stroke. 2016;47:1153-1158 (Year: 2016).*

Time-resolved computed tomography of the liver: retrospective, multi-phase image reconstruction derived from volumetric perfusion imaging, by Fischer et al., Epub. Aug. 31, 2013; DOI: 10.1007/s00330-013-2992-x (Year: 2013).*

D'Esterre et al. "Time-dependent computed tomographic perfusion thresholds for patients with acute ischemic stroke." Stroke 46.12 (2015): 3390-3397.

Heit and Wintermark "Perfusion computed tomography for the evaluation of acute ischemic stroke: strengths and pitfalls." Stroke 47.4 (2016): 1153-1158.

General Electric Company: "CT Perfusion 4D User Manual", Mar. 22, 2018, Retrieved from the Internet: URL:https://customer-doc.cloud.gehealthcare.com/copyDoc/5788560-1EN/1.

International Search Report and Written Opinion dated Apr. 27, 2020 in International Patent Application No. PCT/CA2020/050108 (7 pages).

Extended European Search Report dated Oct. 17, 2022 in European Patent Application No. 20747949.4 (7 pages).

* cited by examiner

Phase with highest HU (Slope Phase 1-2 +
Slope Phase 2-3) /2

Area under TDC

Machine Learning Model
with Deconvolution

SYSTEM AND METHOD FOR GENERATING PERFUSION FUNCTIONAL MAPS FROM TEMPORALLY RESOLVED HELICAL COMPUTED TOMOGRAPHIC IMAGES

CROSS-REFERENCE

This application is a 35 USC § 371 national stage entry of International Patent Application No. PCT/CA2020/050108, filed Jan. 29, 2020, which claims the benefit of U.S. Provisional Patent Application No. 62/798,358, filed Jan. 29, 2019, and the entire contents of each of which are hereby incorporated by reference.

FIELD

Various embodiments are described herein that generally relate to the generation of perfusion functional maps from Time-Resolved Helical Computed Tomography Angiograms.

BACKGROUND

Stroke is a leading cause of morbidity and the third leading cause of death in developed countries. For example, in Canada, there are about 50,000 strokes per year and about 300,000 people living with the effects of stroke. When a person suffers a stroke, a stroke specialist, such as a stroke clinician or a neurologist, must determine the severity of the stroke in order to determine a treatment method, which typically involves some form of recanalization. Time is of the essence for treatment since the longer the person goes without receiving treatment after suffering a stroke, the larger the amount of neurons and synapses that are damaged which makes it increasingly difficult for the person to recover and may result in loss of motor and neural function for the person as well as premature aging.

In order to aid the stroke specialist to determine the severity of the stroke, a typical CT stroke imaging protocol has been developed worldwide. At all centres, an admission non-contrast CT image is acquired to rule out any stroke mimic blood in the brain. Next, at most centres, a contrast enhanced (iodinated inert fluid) single phase CTA (sCTA) is acquired to provide information on the large vessels of he brain, potentially providing vascular occlusion location if present. However, it is not suitable for determining the viability state of tissue. Therefore, to look at the tissue state, another acquisition may be used, CT Perfusion (CTP), in which another dose of an CT contrast agent is used to determine the hemodynamic temporal changes in brain tissue. The changes in brain tissue density over time depend on the changes in iodine concentration which in turn is a reflection of the nature of brain tissue vascularity. While CTP provides valuable information about the viability of brain tissue during, its downsides are that it subjects the patient to increased amounts of harmful X-ray radiation (a dose similar to what a person is subjected to in one year on earth), needs another CT contrast agent injection which has implications for renal failure in some patients, and also requires the acquisition and remote processing of a large amount of imaging data, which requires additional infrastructure and is an added expense to hospitals.

Multiphase CT Angiography (mCTA), which has been developed to assess in pial artery filling (surrogate for collateral efficiency to the ischemic tissue at risk), may represent a compromise between the time to gather data, the quality of the gathered data and reducing the amount of exposure of the person to X-ray radiation and image contrast agent (Menon, et al. 2015). For example, mCTA has been found to improve clot detection versus single phase CTA (Volny et al., 2017) while also using a lower X-ray and image contrast agent dose than when CTP is used. The mCTA imaging protocol also has faster image data acquisition for the whole brain and requires less data processing. However, the interpretation of mCTA imaging data is difficult and subjective as the mCTA imaging data is currently presented to the stroke specialist in a raw format after image reconstruction has been performed and does not look at the state of the tissue, which is crucial for many patients whose stroke onset time is unknown.

Accordingly, the stroke imaging community is still trying to find a balance between the complexity of obtaining and interpreting CT images, achieving high accuracy of diagnosis and selection of the treatment method and minimizing the time to diagnosis and treatment decision.

SUMMARY OF VARIOUS EMBODIMENTS

In accordance with one broad aspect of the teachings provided herein, there is provided a system for providing at least one Computed Tomography Angiography (CTA) perfusion functional map, wherein the system comprises: at least one processor that is configured to: obtain Time Resolved Helical CTA (TRH-CTA) image data; preprocess the TRH-CTA helical image data to generate preprocessed TRH-CTA helical image data; generate time density curve data for a plurality of voxels from the preprocessed TRH-CTA helical image data for an axial imaging slice, where the time density curve data comprise intensity values for different phases of the preprocessed TRH-CTA helical image data arranged sequentially in time; generate the at least one perfusion functional map for the axial imaging slice by at least one of: (1) applying at least one mapping function to different phases of the time density curve data corresponding to the axial imaging slice; (2) applying a deconvolution method to the time density curve data; and (3) applying a non-deconvolution method to the time density curve data; and perform filtering in the spatial domain or the frequency domain on the at least one perfusion functional map; and a display that is coupled to the at least one processor for receiving and displaying the at least one filtered perfusion functional map.

In at least one embodiment, the at least one processor is configured to obtain the TRH-CTA image data by loading TRH-CTA image data from a data store or receiving the TRH-CTA image data from a CT scanner where the TRH-CTA image data was obtained by the CT scanner from a patient after the patient received a bolus of imaging contrast agent.

In at least one embodiment, at least one processor is configured to preprocess the TRH-CTA image data by: generating raw TRH-CTA image by performing reconstruction on the TRH-CTA image data; separating the raw TRH-CTA image data into separate groups of TRH-CTA time series data where each group corresponds to a distinct phase of the TRH-CTA image data; and performing registration on the separate groups of TRH-CTA time series data to align the separate groups of TRH-CTA time series data in 3D space.

In at least one embodiment, the at least one processor is further configured to generate the preprocessed TRH-CTA helical image data by: applying a first threshold to the groups of TRH-CTA time series data to remove or reduce contributions from a skull of the patient to values of the time series data points; and applying a second threshold to the groups of TRH-CTA time series data to remove or reduce contributions from cerebrospinal fluid of the patient to values of the time series data points.

In at least one embodiment, the at least one processor is configured to apply the mapping function to create a delay map for a plurality of pixels corresponding to the axial imaging slice by, for a given pixel, selecting a highest intensity value of the time density curve data for the voxel that corresponds to the given pixel.

In at least one embodiment, the at least one processor is configured to apply the mapping function to create a first blood flow map for a plurality of pixels corresponding to the axial imaging slice by, for a given pixel, determining a slope of the intensity value of the time density curve data over first and second phases of the voxel that corresponds to the given pixel.

In at least one embodiment, the at least one processor is configured to apply the mapping function to create a second blood flow map for a plurality of pixels corresponding to the axial imaging slice by, for a given pixel, determining a slope of the intensity value of the time density curve data over second and third phases of the voxel that corresponds to the given pixel.

In at least one embodiment, the at least one processor is configured to generate a flow average perfusion functional map by averaging the first and second blood flow maps.

In at least one embodiment, the at least one processor is configured to apply the mapping function to create a blood volume map for a plurality of pixels corresponding to the axial imaging slice by, for a given pixel, performing an integral of the time density curve data of the voxel that corresponds to the given pixel.

In at least one embodiment, the at least one processor is configured to apply the mapping function to create a wash-out map for a plurality of pixels corresponding to the axial imaging slice by, for a given pixel, subtracting an intensity value of a third phase from a highest intensity value of all phases of the time density data for the voxel that corresponds to the given pixel.

In at least one embodiment, the at least one processor is configured to apply the deconvolution to the time density curve data corresponding to the axial imaging slice by using an arterial input function.

In at least one embodiment, the deconvolution is implemented based on one of a Fourier transform based deconvolution, standard truncated singular value decomposition (sSVD), block-circulant truncated SVD (bSVD), Tikhonov regularization and sparse perfusion deconvolution (SPD).

In at least one embodiment, the at least one processor is configured to apply the non-deconvolution to the time density curve data by applying a function that doesn't involve deconvolution including one of multiplication, subtraction, division, max slope approach, and the Patlak model.

In at least one embodiment, the at least one processor is configured to apply the mapping function to create a combination map for a plurality of pixels corresponding to the axial imaging slice by, for a given pixel, generating at least two functional maps and then combining the at least two functional maps by: (a) optionally applying coefficients to the at least two functional maps followed by applying a linear or non-linear function to combine the at least two functional maps or (b) by applying a machine learning model to the at least two functional maps.

In at least one embodiment, the machine learning model comprises at least one of a logistic regression model, a decision tree, a support vector machine, principle component analysis, a random forest, and a neural network.

In at least one embodiment, the at least one processor is further configured to apply filtering to the at least one perfusion functional map by applying at least one of: (a) spatial filtering including moving average filtering, 3D Gaussian filtering, bilateral Gaussian filtering followed by a full Gaussian blur, or guided filtering, (b) spectral filtering including bandpass, low pass, high pass or band stop filtering in the frequency domain, or (c) iterative spatial and/or frequency filtering.

In at least one embodiment, the at least one processor is further configured to apply at least one threshold to the at least one perfusion functional map to generate an infarct and/or penumbra output volume for the axial imaging slice and display the infarct and/or penumbra output volume.

In at least one embodiment, the at least one processor is further configured to apply additional filtering after the thresholding to remove small objects including small infarcts that are noise.

In at least one embodiment, the at least one processor is further configured to obtain and display a Non-Contract CT (NCCT) image, a CTA and/or a collateral image for the axial imaging slice.

In accordance with one broad aspect of the teachings provided herein, there is provided a method for providing at least one Computed Tomography Angiography (CTA) perfusion functional map, wherein the method is performed by at one processor and the method comprises: obtaining Time Resolved Helical CTA (TRH-CTA) image data; preprocessing the TRH-CTA helical image data to generate preprocessed TRH-CTA helical image data; generating time density curve data for a plurality of voxels for an axial imaging slice from the preprocessed TRH-CTA helical image data, where the time density curve data comprise intensity values for different phases of the preprocessed TRH-CTA helical image data arranged sequentially in time; generating the at least one perfusion functional map for the axial imaging slice by at least one of: (1) applying at least one mapping function to different phases of the time density curve data corresponding to the axial imaging slice; (2) applying a deconvolution method to the time density curve data; and (3) applying a non-deconvolution method to the time density curve data; performing filtering in the spatial domain or the frequency domain on the at least one perfusion functional map; and outputting, via a display, the at least one filtered perfusion functional map.

In at least one embodiment, the method comprises obtaining the TRH-CTA image data by loading TRH-CTA image data from a data store or receiving the TRH-CTA image data from a CT scanner where the TRH-CTA image data was obtained by the CT scanner from a patient after the patient received a bolus of imaging contrast agent.

In at least one embodiment, the method comprises preprocessing the TRH-CTA image data by: generating raw TRH-CTA image by performing reconstruction on the TRH-CTA image data; separating the raw TRH-CTA image data into separate groups of TRH-CTA time series data where each group corresponds to a distinct phase of the TRH-CTA image data; and performing registration on the separate groups of TRH-CTA time series data to align the separate groups of TRH-CTA time series data in 3D space.

In at least one embodiment, the method further comprises generating the preprocessed TRH-CTA helical image data by: applying a first threshold to the groups of TRH-CTA time series data to remove or reduce contributions from a skull of the patient to values of the time series data points;

and applying a second threshold to the groups of TRH-CTA time series data to remove or reduce contributions from cerebrospinal fluid of the patient to values of the time series data points.

In at least one embodiment, the method comprises applying the mapping function to create a delay map for a plurality of pixels corresponding to the axial imaging slice by, for a given pixel, selecting a highest intensity value of the time density curve data for the voxel that corresponds to the given pixel.

In at least one embodiment, the method comprises applying the mapping function to create a first blood flow map for a plurality of pixels corresponding to the axial imaging slice by, for a given pixel, determining a slope of the intensity value of the time density curve data over first and second phases of the voxel that corresponds to the given pixel.

In at least one embodiment, the method comprises applying the mapping function to create a second blood flow map for a plurality of pixels corresponding to the axial imaging slice by, for a given pixel, determining a slope of the intensity value of the time density curve data over second and third phases of the voxel that corresponds to the given pixel.

In at least one embodiment, the method comprises generating a flow average perfusion functional map by averaging the first and second blood flow maps.

In at least one embodiment, the method comprises applying the mapping function to create a blood volume map for a plurality of pixels corresponding to the axial imaging slice by, for a given pixel, performing an integral of the time density curve data of the voxel that corresponds to the given pixel.

In at least one embodiment, the method comprises applying the mapping function to create a washout map for a plurality of pixels corresponding to the axial imaging slice by, for a given pixel, subtracting an intensity value of a third phase from a highest intensity value of all phases of the time density data for the voxel that corresponds to the given pixel.

In at least one embodiment, the method comprises applying deconvolution to the time density curve data corresponding to the axial imaging slice by using an arterial input function.

In at least one embodiment, the method comprises performing deconvolution based on implemented based on one of a Fourier transform based deconvolution, standard truncated singular value decomposition (sSVD), block-circulant truncated SVD (bSVD), Tikhonov regularization and sparse perfusion deconvolution (SPD).

In at least one embodiment, the method comprises applying the non-deconvolution to the time density curve data by applying a function that doesn't involve deconvolution including one of multiplication, subtraction, division, max slope approach, and the Patlak model.

In at least one embodiment, the method comprises applying the mapping function to create a combination map for a plurality of pixels corresponding to the axial imaging slice by, for a given pixel, generating at least two functional maps and then combining the at least two functional maps by: (a) optionally applying coefficients to the at least two functional maps followed by applying a linear or non-linear function to combine at least two functional maps or (b) by applying a machine learning model to combine at least two functional maps. Preferably, each functional map may be weighted according order of importance, given by the coefficient.

In at least one embodiment, the method comprises implanting the machine learning model by using one of a decision tree, a support vector machine, principle component analysis, a random forest, or a number of neural network options.

In at least one embodiment, the method comprises applying filtering to the at least one perfusion functional map by applying at least one of: (a) spatial filtering including moving average filtering, 3D Gaussian filtering, bilateral Gaussian filtering followed by a full Gaussian blur, or guided filtering; (b) spectral filtering including bandpass, low pass, high pass or band stop filtering in the frequency domain; or (c) iterative spatial and/or frequency filtering.

In at least one embodiment, the method comprises applying at least one threshold to the at least one perfusion functional map to generate an infarct and/or penumbra output volume for the axial imaging slice and display the infarct and/or penumbra output volume.

In at least one embodiment, the method comprises applying additional filtering after the thresholding to remove small objects including small infarcts that are noise.

In at least one embodiment, the method comprises obtaining and displaying a Non-Contract CT (NCCT) image, a CTA and/or a collateral image for the axial imaging slice.

In accordance with one broad aspect of the teachings provided herein, there is provided a non-transitory computer readable medium with program instructions stored thereon that, when executed by at least one processor, cause the at least processor to perform a method for providing at least one Computed Tomography Angiography (CTA) perfusion functional map, wherein the method comprises: obtaining Time Resolved Helical CTA (TRH-CTA) image data; preprocessing the TRH-CTA helical image data to generate preprocessed TRH-CTA helical image data; generating time density curve data for a plurality of voxels for an axial imaging slice from the preprocessed TRH-CTA helical image data, where the time density curve data comprise intensity values for different phases of the preprocessed TRH-CTA helical image data arranged sequentially in time; generating the at least one perfusion functional map for the axial imaging slice by at least one of: (1) applying at least one mapping function to different phases of the time density curve data corresponding to the at least one axial imaging slice; (2) applying a deconvolution method to the time density curve data; and (3) applying a non-deconvolution method to the time density curve data; performing filtering in the spatial domain or the frequency domain on the at least one perfusion functional map; and outputting, via a display, the at least one filtered perfusion functional map.

In at least one embodiment, the non-transitory computer readable medium stores computer code for performing other acts of the any one of the methods described in accordance with the teachings herein.

In accordance with one broad aspect of the teachings provided herein, there is provided a method for providing images used to determine a treatment method for treating a stroke patient, wherein the method comprises: administering a bolus of image contrast agent to the patient; and generating and displaying at least one TRH-CTA perfusion functional map according to any of the acts of the methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 3A-3D show case study results for a single patient in which FIG. 3A is a delay perfusion functional map, FIG. 3B is a flow average perfusion functional map, FIG. 3C is an MR diffusion weighted image and FIG. 3D is an amalgamated histogram of all patients in the case study which may be used to determine an optimal threshold for generating the Delay perfusion functional map.

Figure 1:
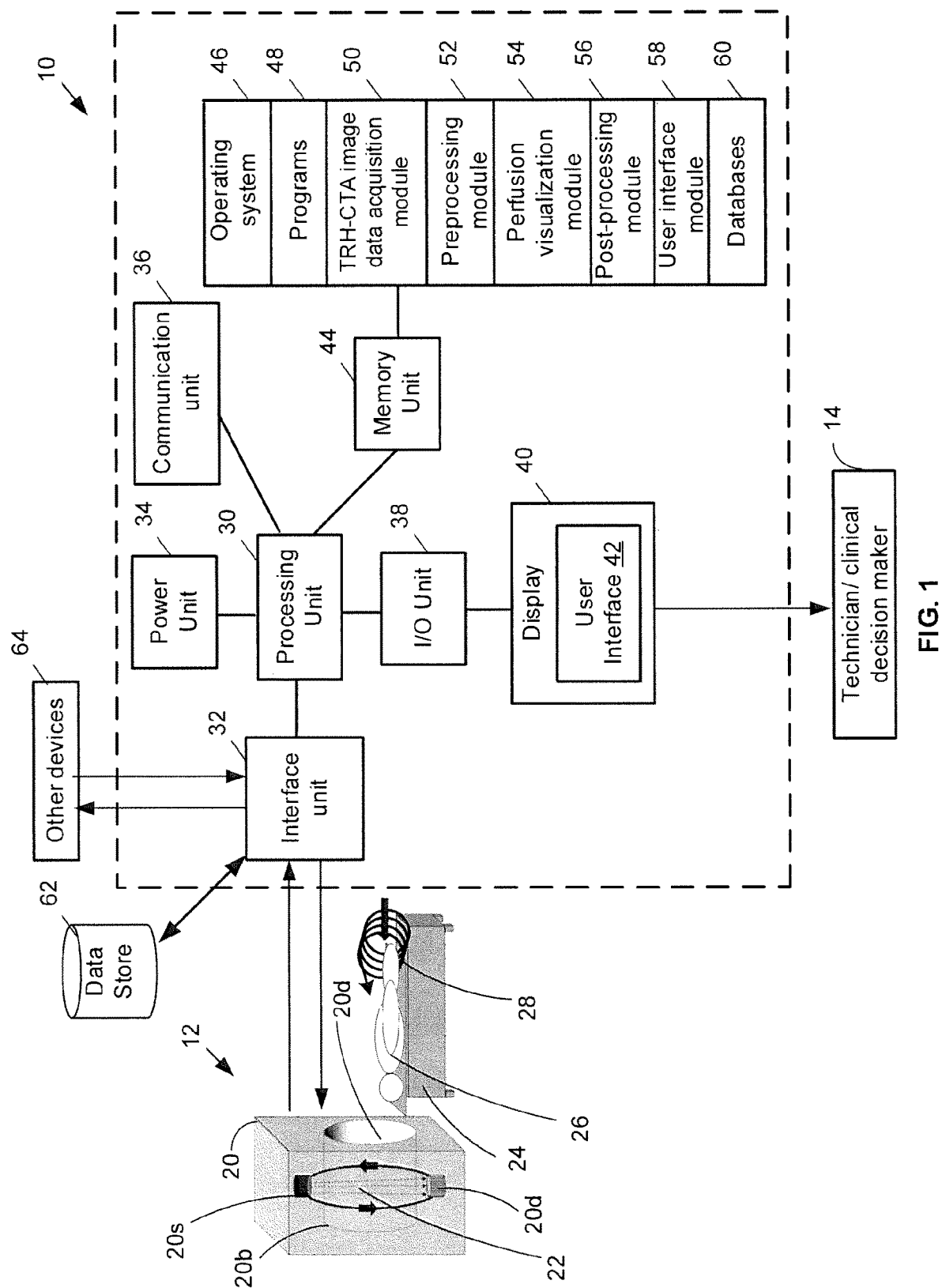
FIG. 1 shows a block diagram of an example embodiment of an imaging system that can perform perfusion visualization based on Time-Resolved Helical Computed Tomography Angiograms (TRH-CTA) image data.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical signal, an electrical connection, an electrical element, or a mechanical element depending on the particular context. Furthermore, certain coupled electrical elements may send and/or receive data.

Unless the context requires otherwise, throughout the specification and claims which follow, the word "comprise" and variations thereof, such as, "comprises" and "comprising" are to be construed in an open, inclusive sense, that is, as "including, but not limited to".

It should also be noted that, as used herein, the wording "and/or" is intended to represent an inclusive-or. That is, "X and/or Y" is intended to mean X or Y or both, for example.

As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" or "approximately" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Similarly, throughout this specification and the appended claims the term "communicative" as in "communicative pathway," "communicative coupling," and in variants such as "communicatively coupled," is generally used to refer to any engineered arrangement for transferring and/or exchanging information. Examples of communicative pathways include, but are not limited to, electrically conductive pathways (e.g., electrically conductive wires, electrically conductive traces), magnetic pathways (e.g., magnetic media), optical pathways (e.g., optical fiber), electromagnetically radiative pathways (e.g., radio waves), or any combination thereof. Examples of communicative couplings include, but are not limited to, electrical couplings, magnetic couplings, optical couplings, radio couplings, or any combination thereof.

In addition, throughout this specification and the appended claims, infinitive verb forms are often used. Examples include, without limitation: "to detect," "to provide," "to transmit," "to communicate," "to process," "to route", and the like. Unless the specific context requires otherwise, such infinitive verb forms are used in an open, inclusive sense, that is as "to, at least, detect", "to, at least, provide", "to, at least, transmit", and so on.

A portion of the example embodiments of the systems, devices, or methods described in accordance with the teachings herein may be implemented as a combination of hardware or software. For example, a portion of the embodiments described herein may be implemented, at least in part, by using one or more computer programs, executing on one or more programmable devices each comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in Python, MATLAB™, Visual Basic, Fortran, C, C++ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media (e.g., a computer readable medium such as, but not limited to, ROM, magnetic disk, optical disc) or a device that is readable by a general or special purpose programmable device. The software program code, when read by at least one processor of the programmable device, configures the at least one processor to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code or program instructions, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage, for example. In alternative embodiments, the medium may be transitory in nature such as, but not limited to, wire-line transmissions, satellite transmissions, internet transmissions (e.g. downloads), media, as well as digital and analog signals, for example. The computer useable instructions may also be in various formats, including compiled and non-compiled code.

The present disclosure provides systems and methods for determining brain perfusion characteristics for a person, such as a patient, using contrast enhanced TRH-CTA imaging data. For example, the perfusion characteristics may be determined for a patient that has recently suffered a stroke. A stroke specialist, such as a stroke clinician or neurologist, can then use the perfusion characteristics to diagnose and determine prognosis and may also inform treatment decisions.

The TRH-CTA imaging data may be determined in accordance with a time-resolved CTA imaging protocol, which comprises a number of sampling periods after the provision of an imaging contrast to a patient. For example, the TRH-CTA imaging protocol may include sampling at two, three, four or more time points, without the need to acquire an additional CT perfusion scan during the acute stroke imaging workup. For ease of illustration, TRH-CTA imaging for three time points will be described hereafter. Three-phase CTA imaging (i.e. three sampling time points) can provide information on parenchymal hemodynamics (i.e. blood flow affecting the function of an organ) distal to an occlusion, similar to CTP. However, TRH-CTA is a less expensive and is a more widely available modality compared to CTP since CTP usually needs expensive post processing software which is only available at tertiary stroke centres and not primary stroke centres. Since TRH-CTA acquires temporal information for at least two different sampling time points, TRH-CTA can provide information in a somewhat similar manner as perfusion CT (Menon et al., 2013 and Frölich et al., 2014). However, TRH-CTA uses less information and requires less processing than perfusion CT.

The TRH-CTA imaging data may be used to generate one or more perfusion functional maps, in accordance with the teachings herein. Furthermore, one or more thresholds may be applied to the perfusion functional maps for predicting various hemodynamic and tissue aspects as well as producing different volume images such as, but not limited to, volume images of infarct and/or penumbral tissue, for example. The stroke specialist can then review the perfusion and/or volume images, as well as the perfusion functional maps and other standard CT images, in order to make a diagnosis and inform recanalization treatment decision.

Studies and testing performed by the inventors have shown that a contrast enhanced TRH-CTA imaging protocol that generates various perfusion functional maps and/or volume images, in accordance with the teachings herein, may be used to provide a stroke imaging workflow that will save time and money while maintaining a similar diagnostic accuracy as current imaging paradigms such as the costly, time inefficient and unstandardized CTP cine scan.

Referring now to FIG. 1, shown therein is a block diagram of an example embodiment of an imaging system 10 that can perform perfusion visualization of TRH-CTA image data. The imaging system 10 is electrically coupled with a CT scanner 12 which is used to acquire the TRH-CTA imaging data for a patient 26. Some of the components of the imaging system 10 can be physically configured as a console that can be used by a user 14, such as a technician, to visualize the TRH-CTA imaging data and obtain one or more perfusions maps and optionally other volume images which can then be used by a stroke specialist to determine a treatment method for the patient when the patient has suffered a stroke, or to detect and monitor other conditions such as epilepsy and/or brain tumours.

The CT scanner 12 comprises a housing 20 with a moveable x-ray source 20s, a radiation detector 20d and a bore 22. The CT scanner 12 further comprises a tray or bed 24 upon which the patient 26 lies down. The tray 24 is moved in an axial direction to place the head of the patient 26 within the bore 22 of the CT scanner 12. The x-ray source 20s generates x-ray beams 20b which are directed towards a portion of the head of the patient 26. The x-ray beams 20b are fan beams for performing volume CT scanning. The x-ray beams 20b travel through the head of the patient 26 and are partially attenuated by softer-tissue and absorbed by denser materials in the head of the patient 26. The x-ray beams 20b that are not absorbed are detected by the x-ray detector 20d. The CT scanner 12 also comprises electronics (not shown) for controlling the operation of the x-ray source 20s and movement of the tray 24 as well as for digitizing the detected x-ray beams to produce CT image data which can be stored and transmitted to another device for further processing.

In accordance with the teachings herein, TRH-CTA can be performed by the CT scanner 12 in which the tray 24 and the x-ray source 20s (and optionally the x-ray detector 20d if it is moveable) are controlled such that as the x-ray source 20s rotates, the tray 24 is moved axially into or out of the bore 22 which results in the CT image data being acquired according to a helical or spiral sampling pathway 28, an example of which is shown for illustration purposes in FIG. 1. This allows for the acquisition of TRH-CTA image data allowing for volume images to be created for different axial slices of the brain of the patient 26. The operation of the CT scanner 12 to perform TRH-CTA imaging is further described by Menon et al. (2015) and is also further discussed herein with respect to FIGS. 2A and 2B. Menon et al. (2015) is hereby incorporated by reference in its entirety.

The imaging system 10 includes a processing unit 30, an interface unit 32, a power unit 34, a communication unit 36, an I/O unit 38, a display 40 that can be used to output a user interface 42 and a memory unit 44. The memory unit 44 comprises software code for implementing an operating system 46, various programs 48, an TRH-CTA image data acquisition module 50, a preprocessing module 52, a perfusion visualization module 54, a post-processing module 56 and one or more databases 60. Certain components of the imaging system 10 can be implemented using a desktop computer, a laptop, a mobile device, a tablet, and the like. The imaging system 10 is provided as an example and there can be other embodiments of the imaging system 10 with different components or a different configuration of the components described herein.

The processing unit 30 controls the operation of the imaging system 10 and is electrically coupled with the CT scanner 12 to receive the helical TRH-CTA image data from the CT scanner 12 as it is being obtained or after it has been obtained by executing the TRH-CTA image data acquisition module 50. In some embodiments, the processing unit 30 can be used to control the CT scanner 12 to perform an TRH-CTA imaging workflow, such as the example workflow shown in FIG. 2A or FIG. 2I. In other embodiments, the processing unit 30 may obtain TRH-CTA image data that has already been obtained and is stored on a data store 62. The data store 62 may comprise one or more databases or may be part of a PACS.

The processing unit 30 can also execute the other modules 52, 54 and 56 for processing the TRH-CTA image data to obtain one or more perfusion functional maps and perform thresholding on these maps for determining various volumes such as the penumbra volume and/or infarct volume, for example. The processing unit 30 may also execute the user interface module 58 for generating the user interface 42 and displaying the user interface 42 on the display 40.

The processing unit 30 can include one or more of any suitable processors, controllers or digital signal processors that can provide sufficient processing power depending on the configuration, and operational requirements of the imaging system 10 as is known by those skilled in the art. For example, the processing unit 30 can include one or more high performance processors. In embodiments where there is more than one processor, each processor may be configured to perform different dedicated tasks. In alternative embodiments, specialized hardware, such as ASICs, can be used to provide some of the functions performed by the processing unit 30.

The interface unit 32 includes various interfaces that allow the imaging system operator 20 to communicate with other devices or computers 64. In some cases, the interface unit 32 can include at least one of a serial port, a parallel port or a USB port that provides USB connectivity. In some embodiments, the interface unit 32 can also include at least one of an Internet, Local Area Network (LAN), Ethernet, Firewire, or digital subscriber line connection or a modem. Various combinations of these elements can be incorporated within the interface unit 32. In the example embodiment shown in FIG. 1, the interface unit 32 is used to send data, such as control data, to the CT scanner 12 and also to receive data, such as TRH-CTA image data, from the CT scanner 12.

The power unit 34 can be any suitable power source that provides power to the various components of the imaging system 10 such as a power adaptor or a rechargeable battery pack depending on the implementation of the imaging system 10 as is known by those skilled in the art.

The communication unit 36 is optional but can be used by the imaging system 10 to communicate with other devices in a wireless fashion. For example, the communication unit 36 can include a radio that communicates utilizing CDMA, GSM, GPRS, Bluetooth or another suitable communication protocol according to communication standards such as IEEE 802.11a, 802.11b, 802.11g, 802.11n or another suitable communication standard. The communication unit 36 can allow the processing unit 30 to communicate wirelessly with the CT scanner 12 or with other devices or computers that are remote from the imaging system 10.

The I/O unit 38 provides one or more ports or other interfaces that allows a user 14, such as an imaging technician or another operator, to control the imaging system 10 by using an input device that is communicatively coupled to the I/O unit 38 to send control input data to the imaging system 10. The I/O unit 38 also provides one or more ports or other interfaces that allows the imaging system 10 to provide outputs to the user 14.

For example, the I/O unit 38 has ports that can be communicatively coupled with at least one input devices such as, but not limited to, at least one of a mouse, a keyboard, a touch screen, a thumbwheel, a track-pad, a track-ball, a card-reader, and the like depending on the particular implementation of the imaging system 10. For ease of illustration, none of these input devices have been shown. The control input data can include, but is not limited to, start and stop commands to control the beginning and end of image data acquisition as well as various parameters that control the timing of the phases of the image data acquisition, the amount of the head of the patient 26 that is imaged, the types of perfusion images to be generated, and the threshold values used to determine the penumbra and/or infarct volumes. In some embodiments, other types of data can be included in addition to the perfusion functional maps such as, but not limited to, one or more of demographics, time from stroke onset to CT, NCCT ASPECTS, and any other admission information such as blood work results, for example. In some embodiments the user interface 42 may provide access to tools that the user 14 can use to enter control input data and perform certain actions.

In some embodiments, the tools may include an acquisition and reconstruction tool (which may be provided by the TRH-CTA image data acquisition module 50 and the pre-processing module 52, for example) that the user 14 can use to acquire the TRH-CTA image data, to separate this data in two, three or more data acquisition phases and align the separated data in 3D space. The functionality of the data acquisition and reconstruction tool corresponds to act 104 of workflow 100 shown in FIG. 2A and may be varied depending on the CT vendor.

In some embodiments, the tools may include a data processing tool (which may be provided by the preprocessing module 52 and/or the perfusion visualization module 54, for example) that the user 14 can use to control the generation of time density curves for each voxel of TRH-CTA image data that is used to generate a perfusion functional map for a given axial slice of the brain of the patient 26. The user 14 may also use the data acquisition processing tool to create one or more perfusion functional maps for the given axial slice. The functionality of the data processing tool corresponds to acts 106, 106a, 106b and 106c of the workflow 100. In some embodiments, the inputs to the data processing tool can be one or more of DICOM, NIFTI, or Matrix-based file formats (one for each sampling time) and/or the outputs of the data processing tool can be matrix-based file formats (e.g. the time-density curves can be stored in a 4-D matrix).

In some embodiments, the tools may include a perfusion post-processing tool (which may be provided by the post-processing module 52 and/or the perfusion visualization module 54, for example) that the user 14 can use to determine infarct and/or penumbra volumes that are derived from the one or more perfusion functional maps that are generated. The user 14 may also use the perfusion post-processing tool to display the infarct and/or penumbra tissue regions in volume images as well as optionally to display other CT images that have been obtained, using known techniques, such as collateral and Non-contrast CT (NCCT) images, for example. In some embodiments, the inputs to the perfusion post-processing tool can be a 4D matrix (e.g. the time-density curves can be stored in a 4-D matrix) and/or the output can be one or more of DICOM, NIFTI, or a matrix-based file formats (e.g. a perfusion map can be stored in a 3-D matrix).

The user 14 may generate one or more of the perfusion images, generate images showing the infarct and/or penumbra volumes as well as optionally generate and show the collateral and Non-contrast CT (NCCT) images, depending on which of the images provide the most useful information so that the stroke specialist can make an accurate diagnosis and select an appropriate course of treatment. Alternatively, some stroke specialists may wish to view all of these images.

The user 14 may generate images showing the infarct and/or penumbra volumes by applying a threshold. The threshold may be determined in different ways. For example, thresholds may be determined from two different cohorts of patients. A first cohort of patients can be used to determine the threshold for infarct tissue (i.e. a volume of tissue that is non-viable even with fast reperfusion) where these patients are those who receive endovascular treatment within 90 minutes of admission CT and achieve quality reperfusion (TICI-2b/3) as defined on the last run of a digital subtraction angiography image (DSA). A second cohort of patients can be used to determine the threshold for penumbra tissue (i.e. a volume of tissue that will infarct without reperfusion) where these patients are those who do not reperfuse (TICI-0). This methodology is explained in more detail in d'Esterre et al. (2015), which is hereby incorporated by reference.

In some embodiments, the tools may comprise the acquisition and reconstruction tool, the data processing tool and the perfusion post-processing tool. In some embodiments, some of these tools may not be available for the user 14 to enter control data as the functionality of at least some of these tools may be preset during manufacturing so that the system 10 operates in a known and controlled manner so that a user 14 cannot enter data which may otherwise cause the system 10 to not operate properly.

As another example, the I/O unit 38 has ports that can be communicatively coupled with at least one output device such as, but not limited to, at least one of a microphone, a speaker, a printer, a display and the like again depending on the particular implementation of the imaging system 10. Only one example of an output device, e.g. the display 40, is shown for ease of illustrative purposes.

The display 40 can be any suitable display that provides visual information depending on the configuration of the imaging system 10. For instance, the display 40 can be a cathode ray tube, a flat-screen monitor and the like if the imaging system 10 is at least partially implemented using a desktop computer. In other cases, the display 40 can be a display that is suitable for a laptop, a tablet or a handheld device such as an LCD-based display and the like when the imaging system 10 is implemented at least partially using these devices.

The display 40 can provide various types of information to the user 14 such as, but not limited to, one or more of patient data, CT scan status, raw TRH-CTA image data, one or more perfusion functional maps, one or more volume images and other types of images such as, but not limited to, NCCT images and collateral images. The patient data can include various information about the patient 26 such as one or more of name, sex, age, medical history and any previous CT images that have been obtained, for example. The patient data can be obtained from a PACS, the databases 60, the data store 62 or one of the devices 64. The perfusion functional maps may be, but are not limited to, one or more of a blood volume map, a blood flow map or other types of perfusion functional maps described herein, for example. The volume images may be, but are not limited to, a penumbra volume image, an infarct volume image or other types of volume images, such as, but not limited to, images of tissue that will infarct based on time from CT to reperfusion (as described in d'Esterre et al., 2015), for example.

In some embodiments, the display 40 can provide this information via the graphical user interface 42, which will have output fields, or output regions where certain information is displayed for the user 14 to see as well as certain input fields where the user 14 may provide certain control input data. For example, the control input data may control how helical TRH-CTA image data is acquired and processed. In some embodiments in which there are tools that are provided for the user 14 to control the operation of the system 10 and the generation of images, these tools may be displayed using the user interface 42. In such embodiments, the tools may include at least one of the acquisition and reconstruction tool, the data processing tool and the perfusion post-processing tool.

The memory unit 44 can include RAM, ROM, one or more hard drives, one or more flash drives or some other suitable data storage elements such as disk drives, etc. The memory unit 44 may be used to store the operating system 46 and programs 48 as is commonly known by those skilled in the art. For instance, the operating system 46 provides various basic operational processes for the imaging system 10 and the programs 46 can include certain system diagnostic tools that can be used to perform troubleshooting on the imaging system 10 as well as other common user applications such as, but not limited to, an email application, and a spreadsheet applications, for example.

The various modules 50, 52, 54, 56 and 58 comprises software code (i.e. program instructions) that when executed, by at least one processor, such as at least one processor of the processing unit 30, for example, includes instructions for performing certain functions as described in further detail below. Accordingly, the processing unit 30 may access the memory unit 44 to load software instructions from any of the programs 48 and/or the various modules 50 to 58 and execute the software instructions in order to operate the imaging system 10 according to a desired fashion or a fashion selected by the user 14.

While some of the modules 50, 52, 54, 56 and 58 will be described as performing certain functions, it should be understood that in alternative embodiments some of these functions may be performed by other modules. In some embodiments, some of the modules 50, 52, 54, 56 and 58 may be combined or further separated into two or more modules. Furthermore, while the modules 50, 52, 54, 56 and 58 are preferably implemented using software in alternative embodiments the functionality of at least one of the modules 50, 52, 54, 56 and 58 may be implemented using an FPGA or application specific circuitry.

The TRH-CTA image acquisition module 50 may be used to obtain the TRH-CTA image data from the CT scanner 12 or from the data store 62. The TRH-CTA image data acquisition module 50 can also load the acquisition parameters used to obtain the TRH-CTA image data as well as data about the geometrical characteristics of the x-ray beams 20b and the x-ray detector 20d so that reconstruction and alignment can be performed on the TRH-CTA image data as described below. In some embodiments, the TRH-CTA image data acquisition module 50 may be used to control the CT scanner 12 to obtain the TRH-CTA image data according to various acquisition parameters which can be used to control the generation of the x-ray beams 20b as well as the motion of the x-ray source 20s and the tray 24 to provide the helical pattern 28 for image data acquisition. Other parameters can be specified such as the sampling rate, the sampling times for obtaining image data for different phases as well as the timing and intensity of the generated x-ray beams 20b. These parameters may be stored in the databases 60 or it may be provided by the user 14 depending on the embodiment.

The preprocessing module 52 may be used to preprocess the TRH-CTA image data. The preprocessing may involve performing TRH-CTA image data acquisition from the patient 26 in real-time or load this data from a data store. The preprocessing may further involve separating the TRH-CTA image data into N groups of time series of image data where each group of time series is for a different phase, and aligning the N series of volume time points in 3D space. In some embodiments, N can be an integer such as 3 or more than 3.

In some embodiments, the preprocessing module 52 may provide the back-end processing capability for the acquisition and reconstruction tool while the user interface module 58 may be used to create a first Graphical User Interface (GUI) for this tool to allow the user 14 to enter control input data for this tool and receive output data related to the preprocessing.

The perfusion visualization module 54 can be used create one or more desired perfusion functional maps. Accordingly, the perfusion visualization module 54 can generate time density curves for the voxels of interest, which can be a subset of voxels or all of the voxels, in a desired perfusion functional map. The perfusion visualization module 54 can then select a mapping function that corresponds to the desired perfusion functional map and apply the mapping function to the time density curves for the voxels of interest to create perfusion values for these voxels. In some embodiments, the perfusion visualization module 54 can also apply some further processing to the voxels of interest in order to remove noise and/or improve the visual contrast of the voxels of interest in the perfusion functional map. For example, the perfusion visualization module 54 can apply spatial filtering, as described at act 108c of method 100, to the perfusion values of the voxels of interest to improve SNR and create a final version of the desired perfusion functional map. In some cases, additional filtering can be performed to remove small infarcts that are noise, as described in further detail with respect to method 100. In an alternative embodiment, which is discussed more with respect to FIG. 2I, the perfusion visualization module 54 can be adapted to perform deconvolution or non-deconvolution with respect to the time density curves.

In some embodiments, the perfusion visualization module 54 may provide the back-end processing capability for the data processing tool while the user interface module 58 may be used to create a second GUI for this tool to allow the user 14 to enter control input data for this tool and receive output data related to the preprocessing.

The post-processing module 56 can be used to create other images, or determine other characteristics such as the penumbra and/or infract volumes, based on one or more of the perfusion functional maps that are created by the perfusion visualization module 54. The post-processing module 56 can also be used for displaying one of more of a perfusion functional map, the penumbra and/or infarct volume images in mL or $cm^3$, or any applicable unit of volume, as well as other types of images such as collateral and/or NCCT images.

In some embodiments, the perfusion visualization module 54 may provide the back-end processing capability for the perfusion post-processing tool while the user interface module 58 may be used to create a third GUI for this tool to allow the user 14 to enter control input data for this tool and receive output data related to the preprocessing.

As described previously, the user interface module 58 can be used to create the user interface 42 which may include various types of GUIs for allowing the user 14 to operate the imaging system 10 as well as various GUIs to allow the user 14 to interact with one or more of acquisition and reconstruction tool, the data processing tool and the perfusion post-processing tool.

The one or more databases 60 can be used to store data for the imaging system 10 such as various system settings, parameter values, and calibration data. The databases 228 can also store other information required for the operation of the programs 48 or the operating system 46 such as dynamically linked libraries and the like. The databases 60 can also store data related to the operation of the TRH-CTA image data acquisition module 50, the preprocessing module 52, the perfusion visualization module 54, the post-processing module 56 and the user interface module 58.

Figure 2A:
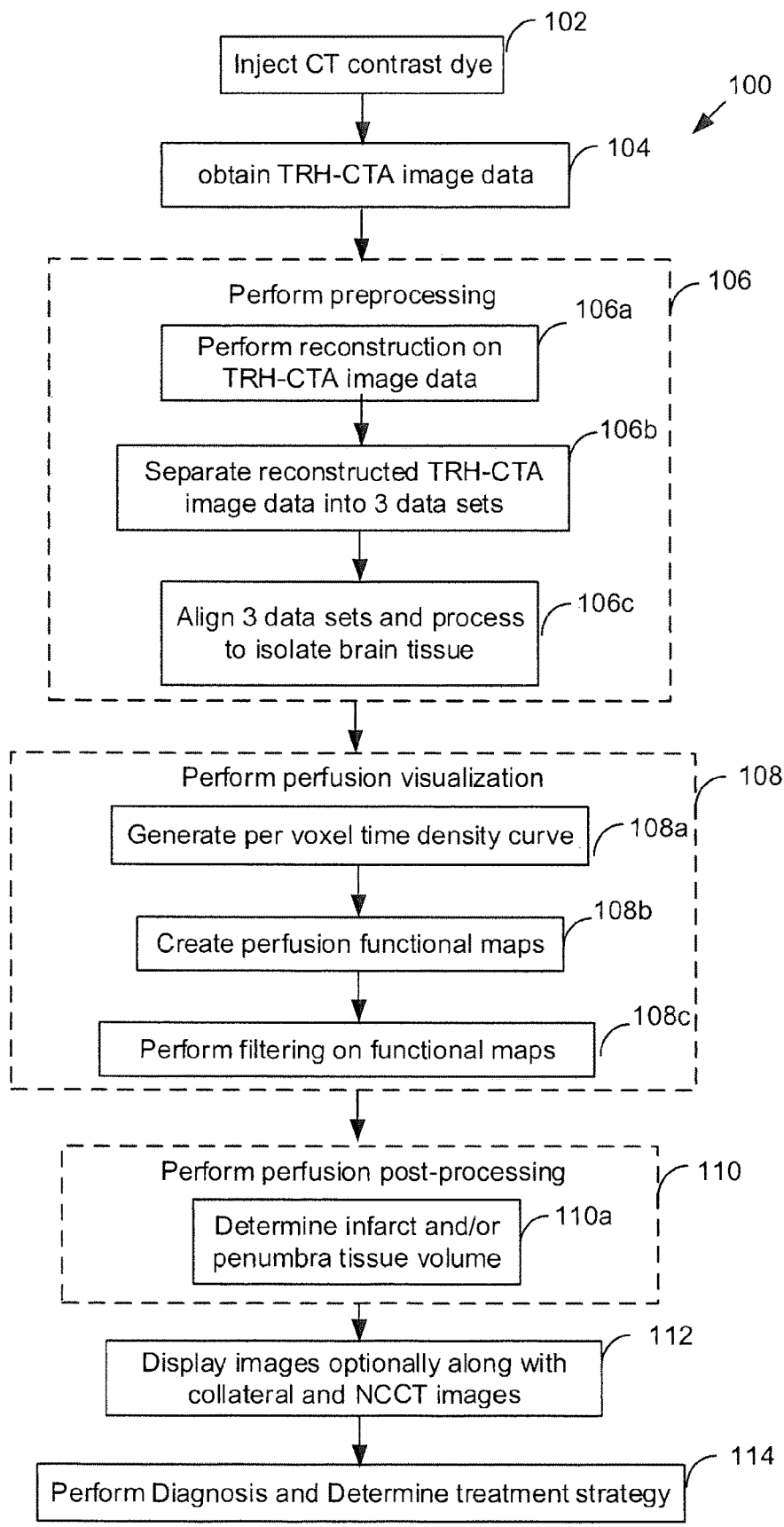
FIG. 2A shows a flow chart diagram of an example embodiment of a method for performing an imaging workflow in accordance with the teachings herein.

Referring now to FIG. 2A, shown therein is a flow chart diagram of an example embodiment of a method 100 for performing a stroke imaging workflow which involves obtaining TRH-CTA imaging data and performing perfusion visualization on the TRH-CTA imaging data. The perfusion visualization may include generating and displaying at least one CTA based perfusion functional map and/or volume images that are derived from one or more TRH-CTA-based perfusion functional maps.

At act 102, the workflow 100 includes injecting a bolus of CT contrast dye into the patient 26. In some embodiments, NCCT image data may be obtained before providing the CT contrast dye to the patient 26. As described previously, the CT contrast dye is an imaging contrast agent that improves the contrast of various structures in the CT image. The CT contrast dye may be an iodine contrast agent or some other suitable chemical solution. The amount and type of CT contrast dye that is given to the patient 26 may be determined according to the amount that will not affect the determination of the perfusion maps, such as 40 to 80 mL, for example.

At act 104, the workflow 100 includes obtaining TRH-CTA image data after the patient received the bolus of imaging contrast agent. At least one processor of the processing unit 30 may be configured to do this. The TRH-CTA image data may be obtained by loading the TRH-CTA image data from a data store, such as the data store 62, or receiving the TRH-CTA image data from the CT scanner 12 in real-time or receiving stored TRH-CTA image data from the CT scanner 12.

Figure 2B:
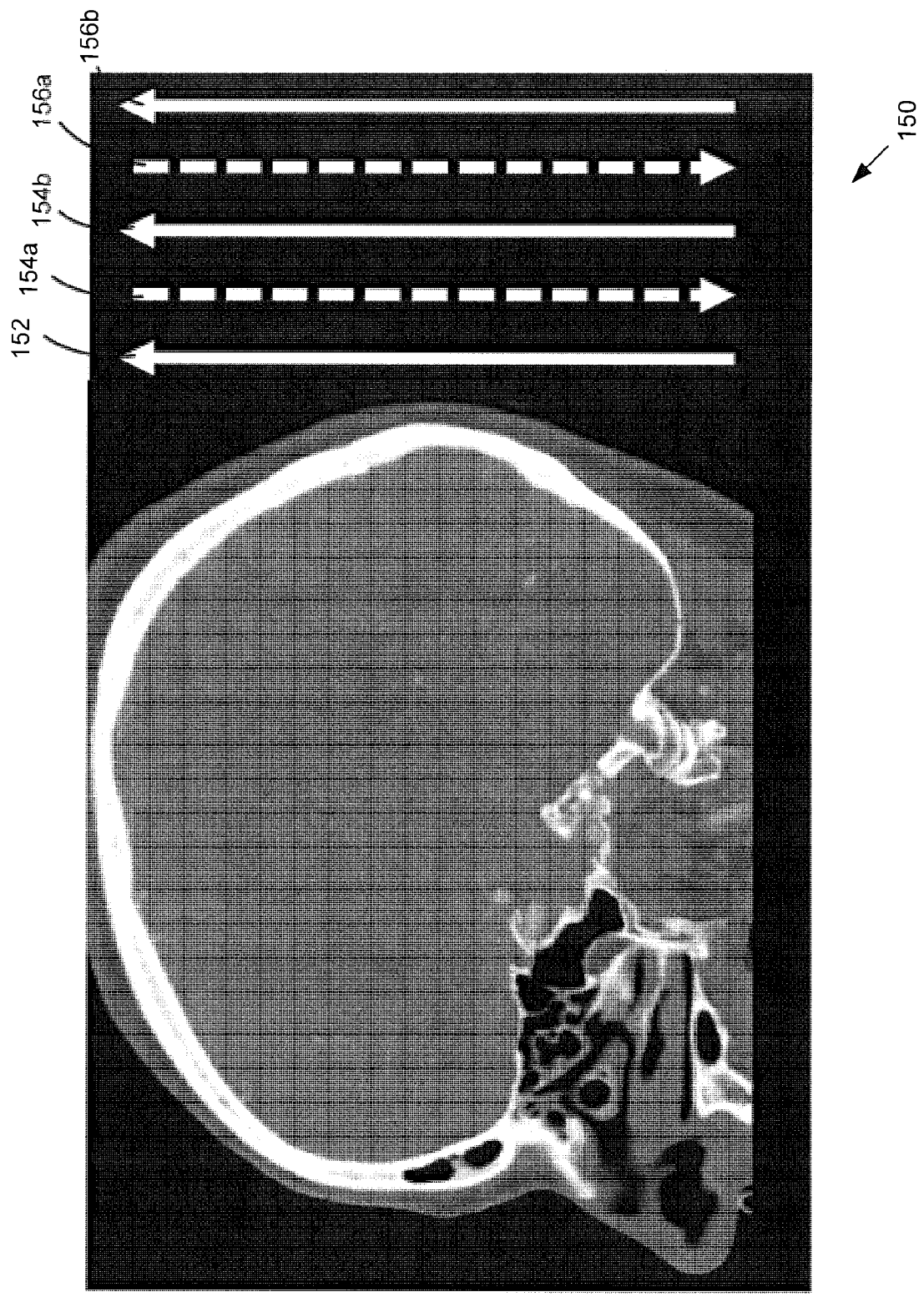
FIG. 2B shows an example of TRH-CTA image data acquisition, with each phase represented by at least one arrow.

Referring now to FIG. 2B, shown therein is an example of an TRH-CTA image data acquisition, with each phase (i.e. time sampling point) represented by at least one arrow. The first phase (solid arrow 152) is the same as in a conventional arch-to-vertex CT angiography. The second phase (solid arrow 154b) and the third phase (solid arrow 156b) are sequential skull base-to-vertex acquisitions performed in the midvenous and late venous phases. The dashed arrows 154a and 156a indicate movement of the CT scanner 12 in between image acquisition phases. The example scan trajectory FIG. 2B shows scanning to obtain three phases of TRH-CTA image data; however, in alternative embodiments, the scan trajectory can be modified to collect two, four or more phases of TRH-CTA image data.

The TRH-CTA imaging technique generates time-resolved cerebral angiograms of brain vasculature from the skull base to the vertex in three phases after contrast material injection. Aortic arch vertex CT angiography performed with a multidetector CT scanner can make up the first phase. Image acquisition can be timed to occur during the peak arterial phase in a normally perfused brain and can be triggered by bolus monitoring. The remaining two time sampling points (e.g. phases) for the example scan trajectory of FIG. 2B are from the skull base to the vertex in the equilibrium/peak venous and late venous phases in a normally perfused brain. The TRH-CTA image data can be acquired according to a certain thickness, such as a 0.5 to 5 mm, 0.5 to 1 mm, of 0.625 mm, for example.

In one example imaging protocol, the first phase of the TRH-CTA imaging from the arch to the vertex may be acquired in less than 7 seconds, with an average dose length product of 700-800 mGy·cm. The second phase may be acquired after a certain delay, such as a delay of 4 seconds for example, that allows for table repositioning for imaging of the skull base of the patient 36. The scanning duration for each additional phase may be set to 3.4 seconds. Thus, the three phases were each 8 seconds apart. However, in alternative embodiments, the TRH-CTA acquisition parameters may be changed for collecting image data at other time points. A total of 80 mL of contrast material (68% ioversol, Optiray 320; Mallinckrodt, St Louis, Mo) may be injected at a rate of 5 mL/sec and followed by a 50-mL normal saline chase at a rate of 6 mL/sec. Generally, a total of 40-80 ml of contrast material may be used. An advantageous feature of the TRH-CTA imaging protocol is that the two additional phases of the TRH-CTA use no additional contrast material and the total radiation dose as per this TRH-CTA imaging protocol was less than that in many established stroke centers.

Referring again to FIG. 2A, at act 106, the workflow 100 includes performing preprocessing on the TRH-CTA image data to generate preprocessed TRH-CTA helical image data. This preprocessing may be done by one or more processors of the processing unit 30. This may be done by first generating raw TRH-CTA image data by performing reconstruction on the TRH-CTA image data at act 106a. For example, continuing again with the TRH-CTA imaging protocol discussed with respect to FIG. 2B, the axial scan images are reconstructed with a certain amount of overlap, such as at 1-mm overlapping sections, and multiplanar reconstructions for axial, coronal, and sagittal images of the circle of Willis may be performed with 3-mm thickness at 1-mm intervals.

Referring again to FIG. 2A, after TRH-CTA image reconstruction, the raw TRH-CTA image data can be separated into separate groups of TRH-CTA time series data where each group corresponds to a distinct phase (e.g. sampling time point) of the TRH-CTA image data acquisition at act 106b. Depending on the protocol used for obtaining the TRH-CTA image data, there is a certain amount of time delay between each group of TRH-CTA time series data. This time delay corresponds to the spacing in time between successive phases of the TRH-CTA imaging protocol. For example, this time delay may be from 8 to 10 seconds. After the separation, the workflow 100 can include performing registration on the separate groups of TRH-CTA time series data to align the separate groups of TRH-CTA time series data in 3D space at act 106c.

Act 106c may also include processing the aligned groups of TRH-CTA time series data to isolate the brain tissue in the data. This can be done by removing any contributions to the time series data due to the skull and/or Cerebrospinal Fluid (CSF) of the head of the patient 26. For example, at least one processor from the processing unit 30 may be configured to apply a first threshold to the groups of TRH-CTA time series data to remove or reduce contributions from the skull of the patient 26 to the values of the time series data points. In addition, at least one processor from the processing unit 30 may be configured to apply a second threshold to the groups of TRH-CTA time series data to remove or reduce contributions from the CSF of the patient 26 to the values of time series data points. The first threshold is generally applied before the second threshold.

At act 108, the workflow 100 includes performing perfusion visualization by using one or more processors of the processing unit 30. This includes generating time density curve data for a plurality of voxels from the preprocessed TRH-CTA helical image data for an axial imaging slice, where the time density curve data comprise intensity values for different phases of the preprocessed TRH-CTA helical image data arranged sequentially in time at act 108a. In at least one embodiment, the time density curve data may be normalized to a baseline value. For example, the time density curve data, which may also be referred to as time attenuation curves (TAC) can be processed to subtract the baseline NCCT HU values for each voxel.

Figure 2C:
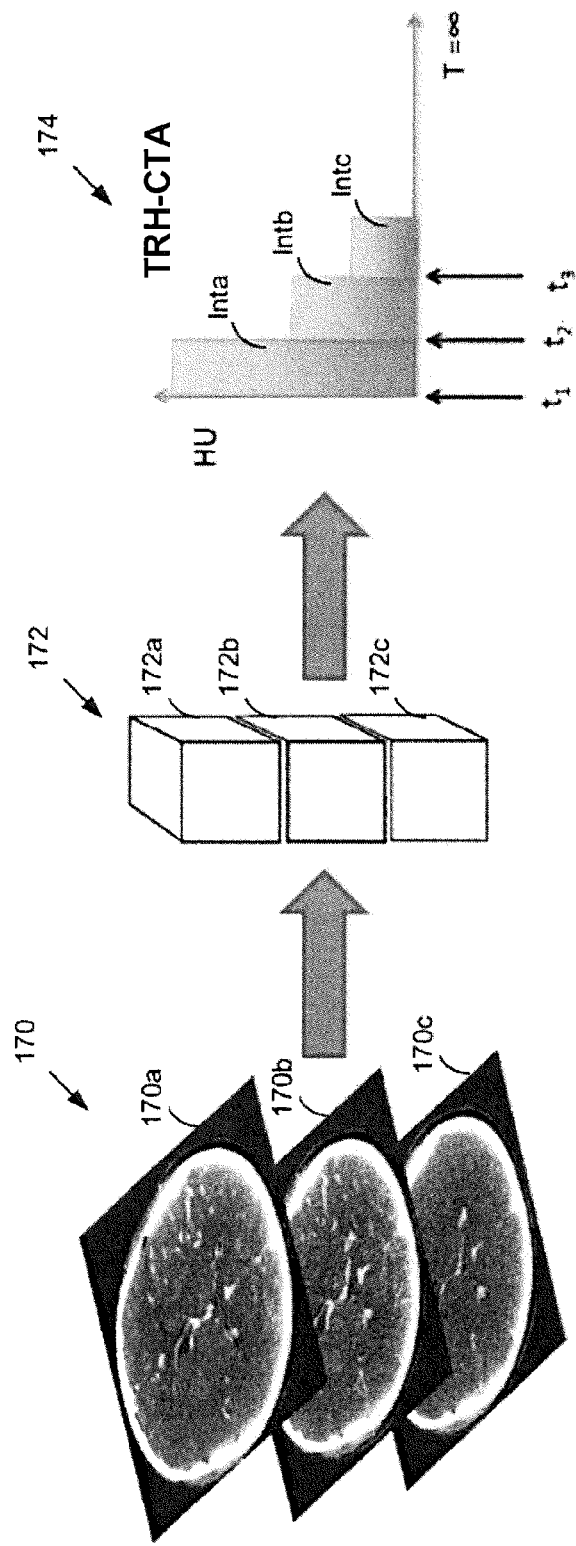
FIG. 2C shows an example of how time density curves can be generated for a given voxel of different TRH-CTA image volumes obtained for an axial imaging slice of a patient's brain.

An example of generating a time density curve is shown in FIG. 2C which shows how a time density curve 174 can be generated for a given voxel 172 of different TRH-CTA image volumes 170a, 170b and 170c obtained for an axial imaging slice 170 of a patient's brain at three different time periods. The voxel 172a corresponds to the image volume 170a for a first phase, the voxel 172b corresponds to the image volume 170b for a second phase and the voxel 172c corresponds to the image volume 170c for a third phase. The intensities of voxels 170a, 170b and 170c, in Houndsfield Units (HU), are shown at times t1, t2 and t3 in the time density curve 174 for the first, second and third phases, respectively.

Figure 2D:
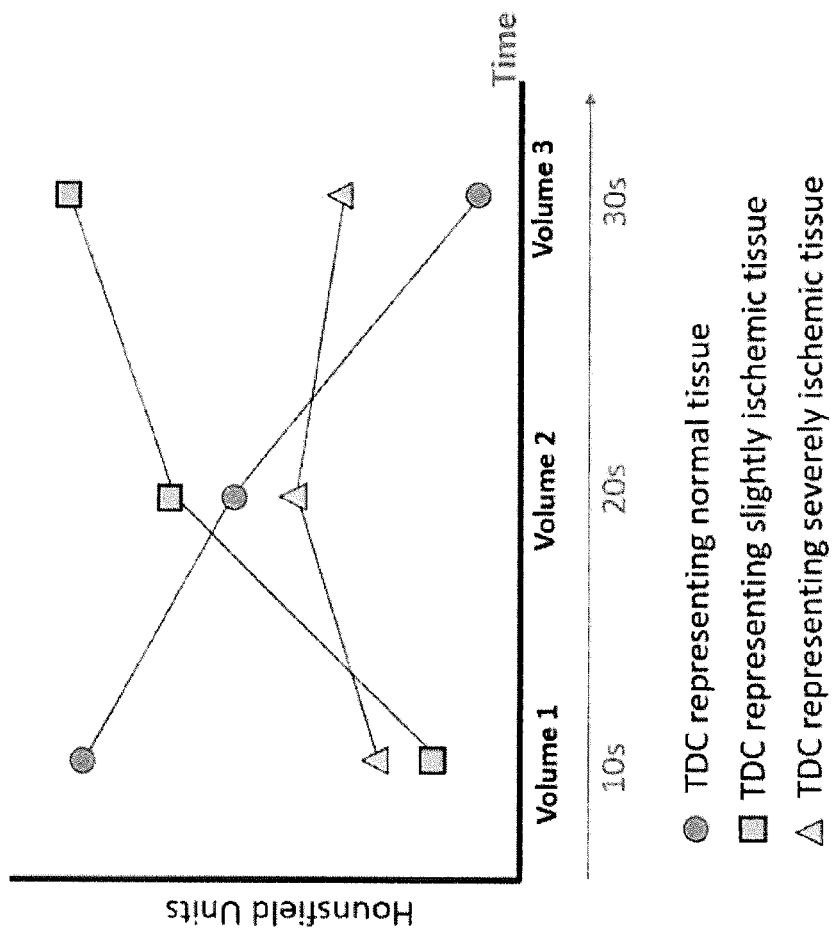
FIG. 2D shows an example of time density curves for a voxel of normal tissue, slightly ischemic tissue and severely ischemic tissue.

Referring now to FIG. 2D, shown therein is an example of several illustrative time density curves for a voxel of normal tissue, slightly ischemic tissue and severely ischemic tissue. As can be seen, different types of tissue will have time density curves with certain characteristics that are different from one another. For example, the intensity of the TRH-CTA image data decreases across phase for normal tissue, increases across phase for slightly ischemic tissue and is somewhat flat or rounded for severely ischemic tissue. This allows for the location of damaged tissue to be determined by looking for these characteristics in the time density curves or in other data derived from the time density curves such as in perfusion functional maps.

Accordingly, after generating the time density curves for the voxels of interest, at least one perfusion functional map for an axial imaging slice may be generated, in accordance with the teachings herein, by applying at least one mapping function to different phases (i.e. different time points) of the time density curve data corresponding to the axial imaging slice at act 108b.

Figure 2E:
FIG. 2E shows an example of a delay perfusion functional map showing highest intensity values for time density curve data for an axial imaging slice of a patient's brain.

In at least one embodiment, the perfusion visualization may include applying a mapping function using at least one processor of the processing unit 30 to create a perfusion functional map which is a delay map for a plurality of pixels corresponding to the axial imaging slice. This can be done by, for a given pixel, selecting a highest intensity value of the time density curve data for the voxel that corresponds to the given pixel. For instance, FIG. 2E provides an example of a delay perfusion functional map.

In at least one embodiment, the perfusion visualization may include applying a mapping function using at least one processor of the processing unit 30 to create a perfusion functional map which is a first blood flow map for a plurality of pixels corresponding to the axial imaging slice. This can be done by, for a given pixel, determining a slope of the intensity value of the time density curve data over first and second phases of the voxel that corresponds to the given pixel.

In at least one embodiment, the perfusion visualization may include applying a mapping function using at least one processor of the processing unit 30 to create a perfusion functional map which is a second blood flow map for a plurality of pixels corresponding to the axial imaging slice. This can be done by, for a given pixel, determining a slope of the intensity value of the time density curve data over second and third phases of the voxel that corresponds to the given pixel.

Figure 2F:
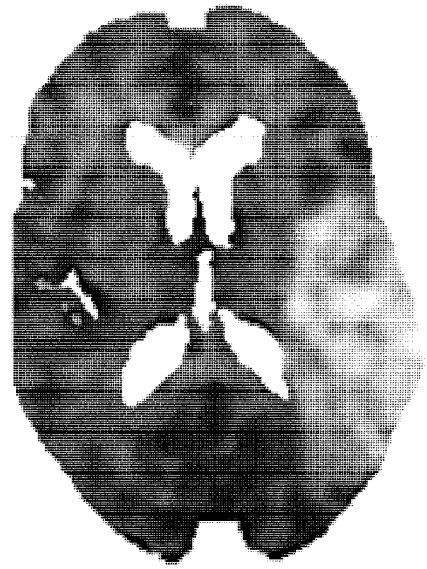
FIG. 2F shows an example of a blood flow perfusion functional map for an axial imaging slice of a patient's brain.

In at least one embodiment, the perfusion visualization may include applying a mapping function using at least one processor of the processing unit 30 to create a perfusion functional map which is a flow average perfusion functional map for a plurality of pixels corresponding to the axial imaging slice. This can be done by, for a given pixel, averaging the first and second blood flows, described above, that correspond to the given pixel. For instance, FIG. 2F shows an example of a blood flow perfusion functional.

Figure 2G:
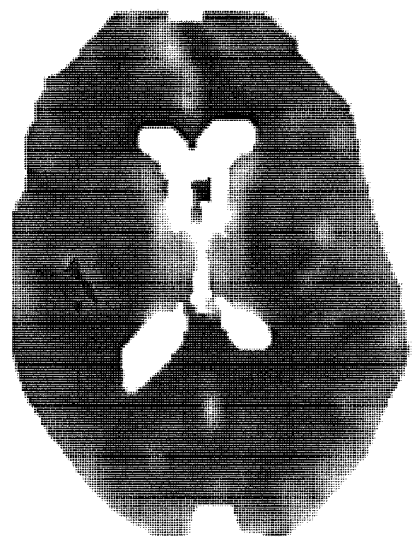
FIG. 2G shows an example of a blood volume perfusion functional map for an axial imaging slice of a patient's brain.

In at least one embodiment, the perfusion visualization may include applying a mapping function using at least one processor of the processing unit 30 to create a perfusion functional map which is a blood volume map for a plurality of pixels corresponding to the axial imaging slice. This can be done by, for a given pixel, performing an integral of the time density curve data of the voxel that corresponds to the given pixel. For instance, FIG. 2G shows an example of a blood volume perfusion functional map.

In at least one embodiment, the perfusion visualization may include applying a mapping function using at least one processor of the processing unit 30 to create a perfusion functional map which is a washout map for a plurality of pixels corresponding to the axial imaging slice. This can be done by, for a given pixel, subtracting an intensity value of a third phase from a highest intensity value of all phases of the time density data for the voxel that corresponds to the given pixel.

In some embodiments, the perfusion visualization may include generating any combination of the aforementioned the perfusion functional maps. For example, in some embodiments, the perfusion visualization may include applying a mapping function using at least one processor of the processing unit 30 to create a perfusion functional map which is a combination map for a plurality of pixels corresponding to the axial imaging slice. This can be done by, for a given pixel, combining any two or more of the aforementioned mapping functions in a linear or nonlinear fashion to obtain a combination map. Such combination maps may allow for a higher accuracy when determining the final infarct volume.

The combination functional maps can be obtained in a variety of different ways. For example, two or more functional maps can be combined by pixel-by-pixel subtraction, addition, multiplication or division which may in some cases include applying coefficients to one or more of the functional maps. The coefficients may be determined by using a machine learning model such as a logistic regression model, for example. Other types of machine learning models that may be used include a decision tree, a support vector machine, principle component analysis, a random forest, and a neural network, for example. The machine learning models are trained using a training data set and known outcomes, and then the trained machine learning model is used to predict outcomes for new patients, e.g. such as in generating an optimized combination perfusion map that may then be used to determined infarct or other items of interest. Alternatively, statistical measures (e.g. mean, median, mode, standard deviation, and skewness), integration, deconvolution, normalization, and differentiation may be used on one or more of the perfusion maps.

An example of an embodiment which uses a logistic regression model for generating a combination functional map is provided in equation (1) and described in further detail in the image processing section of Study #2. In using logistic regression, a set of initial perfusion maps is first selected, coefficients are applied to each perfusion map and the perfusion map along with the coefficients are then applied to a logistic regression model (which is in the form of an equation). Accordingly, the initial functional maps are taken as inputs and calculations are done on a voxel-by-voxel basis according to a function (e.g. equation 1) to generate the combination functional map. For example, equation (1) is based on a backwards step-wise logistic regression model that was trained to create a combination map. The logistic regression model takes the initial (e.g. base) maps as an input and generates a new logistic regression map as the output. This calculation is done on a voxel-by-voxel basis. The training generally involves using many different initial functional maps to vary the values of the coefficients and a scaling constant generating maps using a set of training images to determine a set of values for A, B, C, D and E to improve the discriminatory ability of the linear regression model to distinguish between certain conditions at a voxel level such as infarction and non-infarction. In this example, the backwards step-wise logistic regression model was used to avoid over-fitting the model to the training data. However, for larger training data sets more complex machine learning models may be used to generate the combination functional map.

Figure 2H:
FIG. 2H shows an example of a combination perfusion functional map for an axial imaging slice of a patient's brain that was generated by applying several functional maps as input to a machine learning model.

An example of a perfusion functional map for an axial imaging slice of a patient's brain that is generated by machine learning (i.e. logistic regression) is shown in FIG. 2H.

After a perfusion functional map is generated, it may be further processed to increase the signal to noise ratio and provide more useful information to the stroke specialist so that they may make the proper diagnosis and select the proper course of treatment when reviewing the one or more perfusion maps that are generated. For example, filtering at act 108c of method 100 may be applied to a perfusion functional map after it is initially generated in order to smooth out the perfusion function map. The filtering may be done in the spatial domain or the frequency domain. In at least one embodiment, the filtering may involve applying spatial filtering such as bilateral Gaussian filtering. In such embodiments, a full Gaussian blur (e.g. with a standard deviation of 3×3 pixels) or a 3D Gaussian filter may be applied thereafter. An another example, in at least one embodiment, a guided filter may be used for spatial filtering. In alternative embodiments, other spatial filters that may be used include, but are not limited to, moving average, Gaussian, bilateral Gaussian). Alternatively, spectral filtering may be used such as, but not limited to, bandpass, low pass, high pass, and band stop filtering, for example. In at least one embodiment, the spatial and/or frequency filtering is applied iteratively.

In some embodiments, the filtering may also include performing additional filtering that removes small infarcts that are noise. This additional filtering may act as a small-object removal algorithm by using texture features of the smoothed functional map to improve the accuracy of identifying the main regions of brain death. For example, this additional filtering may be performed by finding the sizes of all objects highlighted by the thresholds, and then removing these objects based on the width of the Gaussian blur filter. The optimization of the removal of small infarcts may also be done iteratively.

At act 110, the workflow 100 includes performing perfusion post-processing on at least one of the perfusion maps that were created at act 108. For example, this post-processing may involve determining the infarct and/or the penumbra tissue volume from one of the perfusion maps at act 110a, such as from preferably the delay perfusion map. This may done by applying a threshold to at least one of the functional maps generated at act 108. The threshold may be determined as explained previously. The determined penumbra and/or infarct volumes may then be shown in other volume images in which the penumbra and/or infract tissue portions of the volume images are shown in different colors and/or outlined or otherwise highlighted compared to surrounding tissue.

At act 112, the workflow 100 includes displaying the one or more perfusion maps as well as the penumbra and/or infarct volume images via the user interface 42 on the display 40. In some embodiments, act 112 can also include displaying collateral images and/or NCCT images.

At act 114, the stroke specialist can review the displayed images in order to perform a diagnosis and determine a treatment strategy. For example, the stroke specialist may diagnose the severity of the stroke and determine whether it is possible to save the penumbra tissue. To aid in this diagnosis, the method 100 may include another act in which the fraction of "core tissue" divided by "the penumbra" is determined and provided as a metric, since this shows how much tissue cannot be saved versus how much tissue can be saved. If it is possible to save a sufficient amount of the penumbra then the stroke specialist may determine that the patient should receive an intravenous tissue plasminogen activator or a suitable endovascular therapy.

Figure 2I:
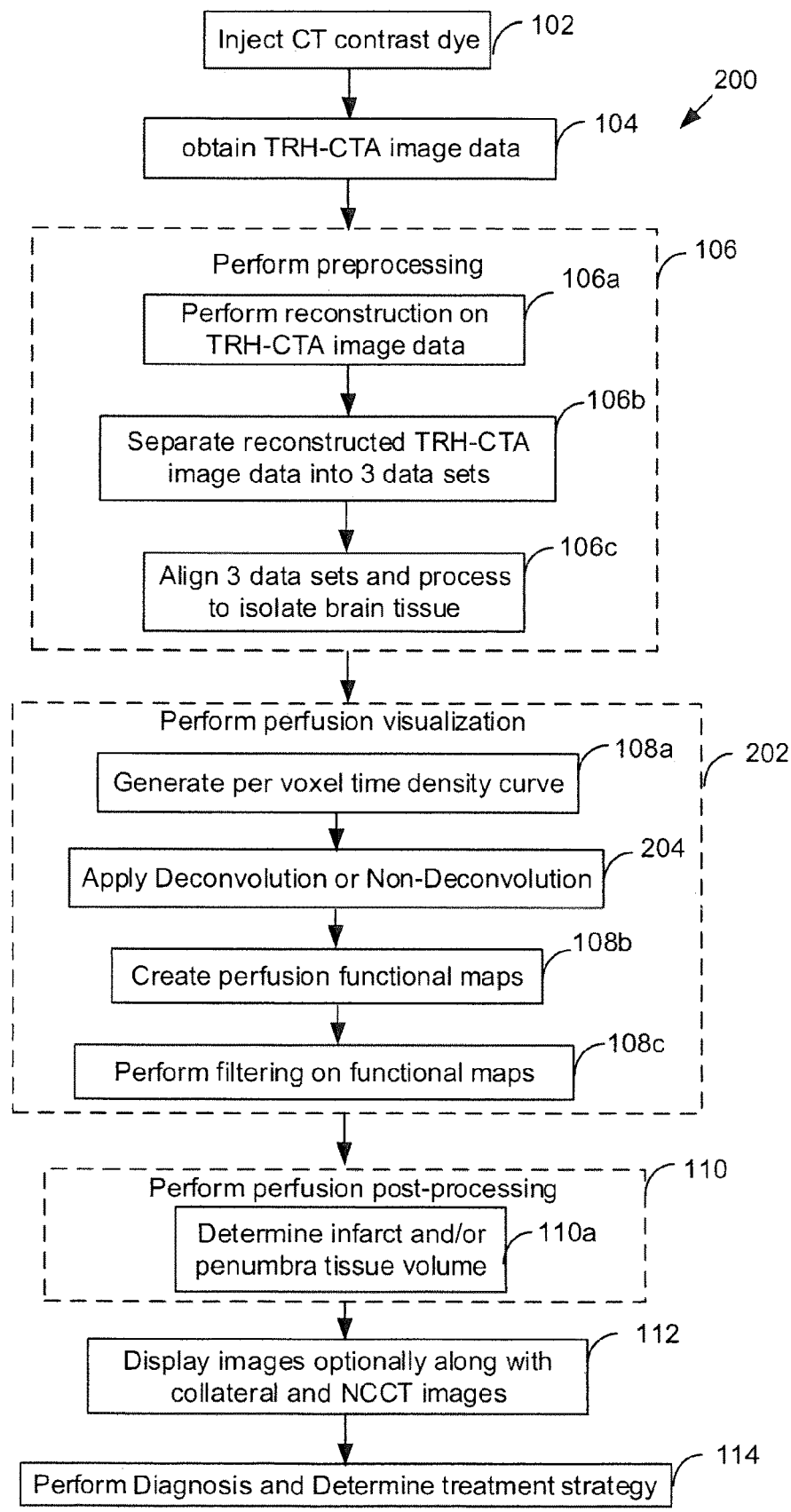
FIG. 2I shows a flow chart diagram of another example embodiment of a method for performing an imaging workflow in accordance with the teachings herein.

Referring now to FIG. 2I, shown therein is a flow chart diagram of an example of an alternative embodiment of embodiment of a method 200 for performing an imaging workflow in accordance with the teachings herein. The method 200 is similar to the method 100 except for having a modified technique for performing perfusion visualization in which deconvolution and/or non-deconvolution is optionally applied to the time density curve at act 204 after the time density curves are generated at act 108*a*. Accordingly, there can be at least one of: (a) one or more perfusion maps generated from the time density curve data as explained for method 100, (b) one or more perfusion maps generated after applying a deconvolution method to the time density curve data and (c) one or more perfusion maps generated after applying a non-deconvolution method to the time density curve data.

Various deconvolution and/or non-deconvolution approaches can be applied to the time density curves to generate deconvolved and/or non-deconvolved to generate one or more functional maps. For example, these functional maps may be those described previously for act 108*b* of method 100 including at least one of a delay map, blood flow maps based on differences in data obtained at different phases, a flow average perfusion functional map, a blood volume map and a washout map. Alternatively, or in addition thereto, the deconvolved/non-deconvolved data may be used to generate at least one of a time to peak (TTP) or T0 map, area under the time density curve, the slope for the first and second time points, a mean transit time (MTT) map, cerebral blood flow (CBF) and cerebral blood volume (CBV) (d'Esterre et al., 2015; Konstas et al., 2009).

The deconvolution method that is used may be based on one of a Fourier transform based deconvolution, standard truncated singular value decomposition (sSVD) (Fang et al., 2015), a block-circulant truncated SVD (bSVD), Tikhonov regularization and sparse perfusion deconvolution (SPD), for example. Each deconvolution method works to different levels of accuracy and have different amounts of computation time.

In deconvolution, these techniques are used to remove the delay and dispersion of the contrast blood that occurs before the reaching the tissue of interest (i.e. the stroke area). This way, a more hemodynamically accurate interpretation of the tissue blood flow can be achieved. Accordingly, the particular deconvolution method is applied along with the selection of an Arterial Input Function (AIF) from the Internal Carotid Artery (ICA) (d'Esterre et al., 2015) such as the basilar artery or contralateral ICA using a 2 voxel×2 voxel (in-slice) region-of-interest (ROI). The AIF is explained in more detail in the image processing section for Study #2.

For non-deconvolution, some example techniques in the context of perfusion imaging are any methods that do not use a convolution operator such as, but not limited to, multiplication, subtraction, division, max slope approach, and the Patlak model, for example (Abels et al., 2010; Horn et al., 2009).

It should be noted that method 200 may be further modified in at least one alternative embodiment to use machine learning, such as a logistic regression model, for generating a combination perfusion map at act 108*b* as was described for method 100. For, example act 108*b* can result in perfusion functional maps that are created by at least one of: (1) applying a mapping function to the time density curve data without deconvolving or non-deconvolving; (2) applying deconvolution to the time density curve data and (3) applying non-deconvolution to the time density curve data. The generated functional maps can then be input to the machine learning algorithm, which generates the best combination perfusion functional map by applying weighting factors to all of the input maps. A check for collinearity of the various input maps may be performed to avoid providing redundant data to the machine learning model. The combination perfusion functional map can be considered as being a probabilistic map for tissue outcome. Thresholds can then be applied to the combination perfusion functional map to obtain volumes of infarct and/or penumbra to estimate what tissue will die with and without reperfusion. As the machine learning algorithm is trained on more data the weighting factors will change and may eventually create patient specific maps when the machine learning algorithm is trained on enough patients with the same demographics and the same type of stroke such that there may be completely different combination functional maps for different sub-sets of patients.

Study #1

A study was performed to determine whether TRH-CTA image data can be used to provide perfusion maps upon which thresholds can be applied to predict the final infarct volume.

The study was performed on 44 stroke patients with occlusion that was visible on CTA. The inclusion criteria for these patients in the study were: (a) the patients presented to the emergency department with symptoms that were consistent with ischemic stroke, (b) the patients were older than 18 years, and (c) the baseline imaging included TRH-CTA imaging performed within 12 hours of stroke symptom onset and initiated before recanalization therapy. Patients were excluded from the study if: (a) an intracranial hemorrhage was identified in the baseline CT, (b) there was a previous moderate to large stroke in the ipsilesional hemisphere, (c) the modified Rankin scale (mRS) score was greater than 2 at baseline; (d) the patient was unable to undergo CT angiography because of recent estimated creatinine clearance of less than 60 mL/min, contrast material allergy or other reasons, (e) the patient participated in another study that resulted in the patient receiving an investigational drug or therapy; and (f) any the patient had a terminal illness (i.e. the patient was not expected to survive longer than 1 year).

The patients were acutely imaged using the three-phase TRH-CTA imaging protocol (the temporal sampling was 8 seconds). MR diffusion weighted imaging (DWI) between 24-48 hours was used to measure the final infarct volume. The TRH-CTA perfusion functional maps were filtered using a 3D Gaussian blurring technique. Two perfusion functional maps, a Delay perfusion functional map and a Flow Average perfusion functional map, were generated for all patients in the study.

A Receiver Operating Characteristic (ROC) curve was generated for the merged patient data, comparing infarct vs. normal tissue. Thresholds were determined using the ROC curves by optimizing for sensitivity and specificity. This involved performing ROC analysis on a voxel-by-voxel basis for all patients in the study, which basically combined all voxels in all of the patients' perfusion maps into a single vector, and divided them into "infarct" vs "healthy". This is represented by the histogram in FIG. 3D. Then, a threshold was optimized between those two distributions by maximizing specificity and sensitivity equally. This can be done by generating the ROC curves by recording specificity and sensitivity for thresholds moving from left to right across the two distributions, in small increments. At a certain point, the sensitivity and specificity are maximized, which is the optimal threshold.

Another metric was implemented by comparing individual infarct volumes directly (on a patient-by-patient basis). This gives another performance measure (e.g. accuracy in terms of mL). For example, the lesions within the patient cohort may be binned into size ranges (i.e. 1 ml to 5 ml, 5 ml to 10 ml, etc.) to determine an accuracy vs. infarct volume size relationship. This is where the filtering to remove small-infarct regions may be done.

Figure 3C:
Figure 3B:
Figure 3A:
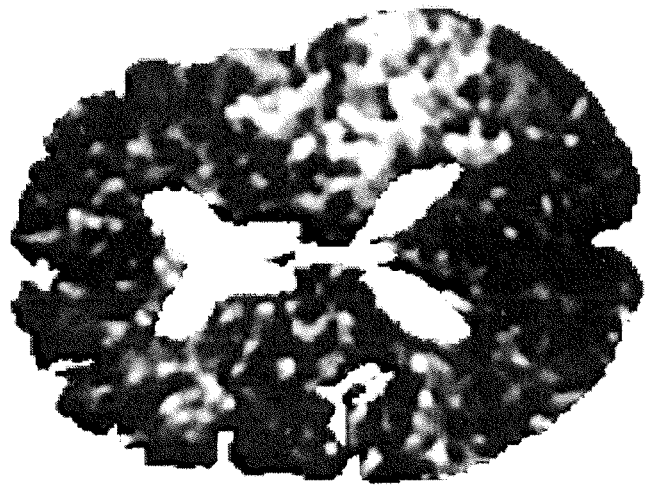
Figure 3D:
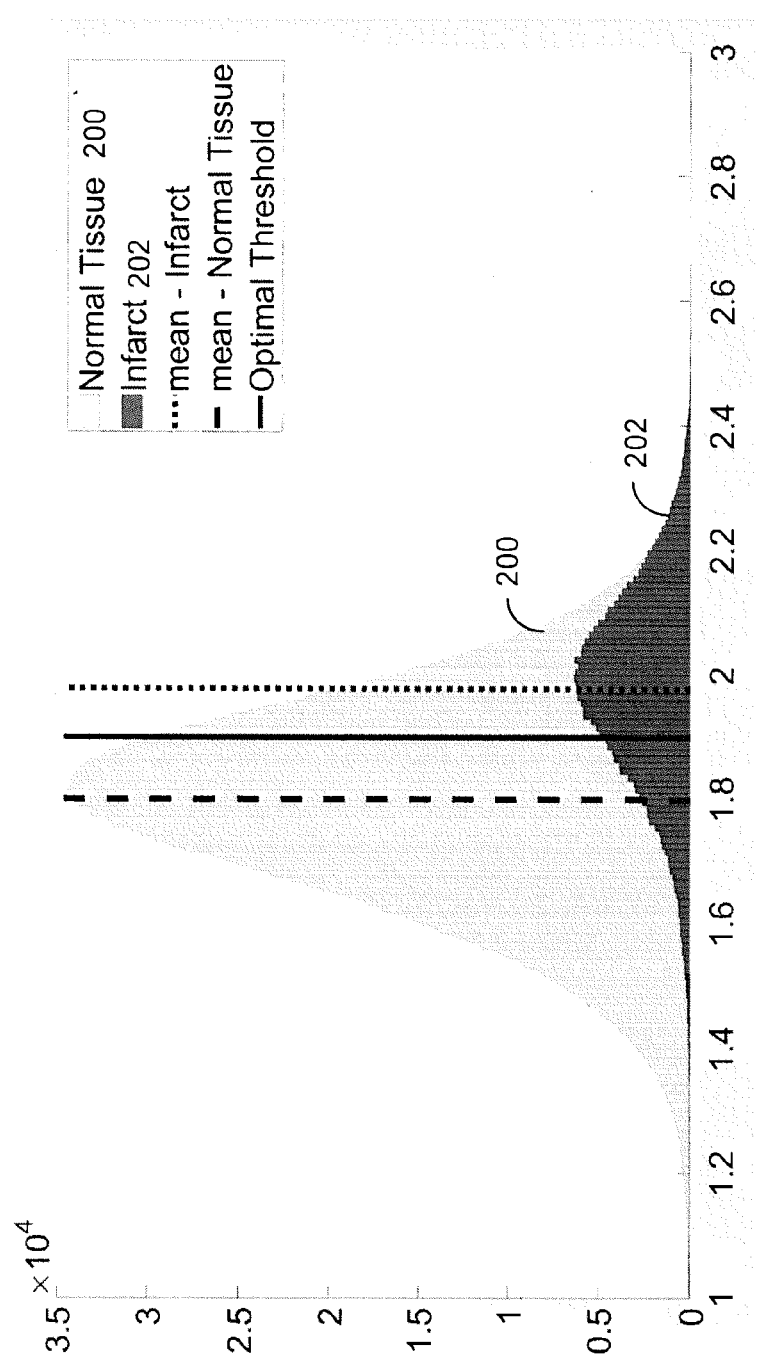

Referring now to FIGS. 3A-3D, shown therein are case study results for a single patient in the study. FIG. 3A is a delay perfusion functional map, FIG. 3B is a flow average perfusion functional map, and FIG. 3C is an MR diffusion weighted image. FIG. 3D is an amalgamated histogram of all patients in the case study which may be used to determine an optimal threshold for generating the Delay perfusion functional map as was just explained.

The "Delay" map generated an ROC curve with an Area-Under-Curve (AUC) of 0.82 (Sensitivity=0.74, Specificity=0.76). The "Flow Average" map generated an ROC curve with an Area-Under-Curve (AUC) of 0.76 (Sensitivity=0.72, Specificity=0.73).

Therefore, the proposed "Delay" and "Flow Average" perfusion functional maps determined from the TRH-CTA image data predicted final infarct volume to a high degree of accuracy, which is close to CTP accuracies reported in the literature (d'Esterre et al., 2015). These results show the capability of the TRH-CTA protocol to generate quantitative perfusion functional maps which will be useful for non-tertiary centers that do not have access to expensive post-processing software.

Figure 4C:
FIGS. 4A-4C show an example of pairs of perfusion functional maps determined for a patient where the first column of images (FIG. 4A) are obtained using the CTP framework, the second column of images (FIG. 4B) are obtained using the TRH-CTA framework described in accordance with the teachings herein and the last column of images (FIG. 4C) are 24 hour diffusion weighted images (DWI).
Figure 4C:
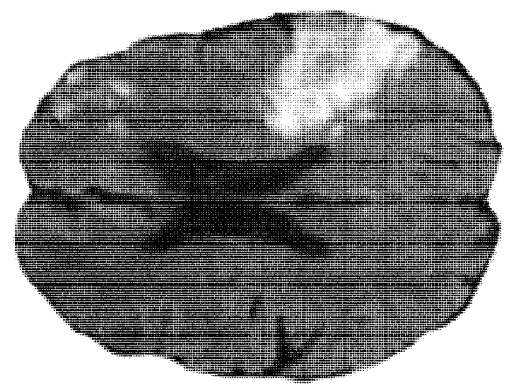
Figure 4B:
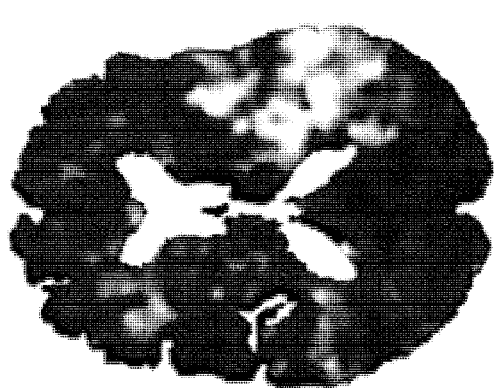
Figure 4B:
Figure 4A:
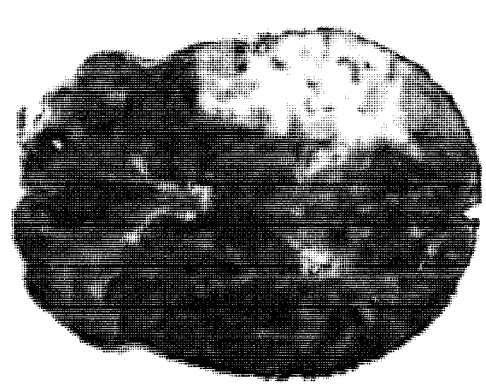
Figure 4A:
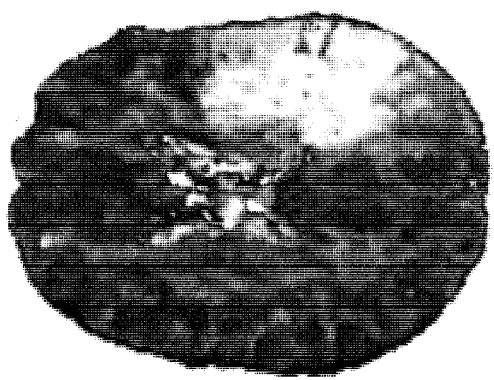

Referring now to FIGS. 4A-4C, shown therein are examples of pairs of perfusion functional maps determined for a patient where the first column of images (FIG. 4A) are obtained using the CTP framework, the second column of images (FIG. 4B) are obtained using the TRH-CTA framework described in accordance with the teachings herein and the last column of images (FIG. 4C) are 24 hour diffusion weighted images (DWI). FIGS. 4A-4C. The patient was an ischemic stroke patient with a large ischemic lesion from a left middle cerebral artery occlusion. At admission CT perfusion (CTP) "T0" functional perfusion imaging was performed (see FIG. 4A) and is shown in two slices, and temporally resolved helical CTA (TRH-CTA) derived perfusion "Delay" maps were obtained (see FIG. 4B), while 24 hour diffusion weighted images (DWI) are shown (see FIG. 4C) after successful fast and quality recanalization (removal of clot). The bright area on the DWI represents dead tissue (infarct) which correlates with the brighter values on the CTP and TRH-CTA functional images. Both the CTP and TRH-CTA correlates with final infarct volume.

Figure 5C:
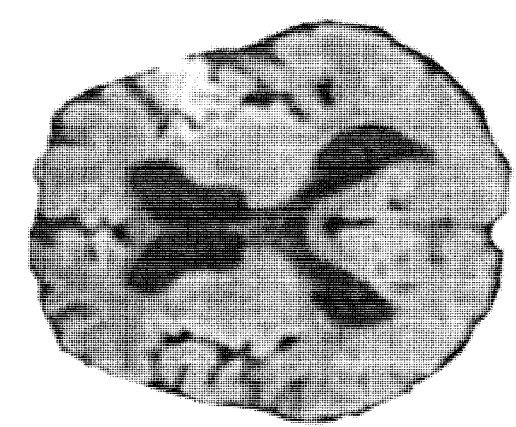
FIGS. 5A-5C show an example of pairs of perfusion functional maps determined for a second patient where the first column of images (FIG. 5A) are obtained using the CTP framework, the second column of images (FIG. 5B) are obtained using the TRH-CTA framework described in accordance with the teachings herein and the last column of images (FIG. 5C) are 24 hour diffusion weighted images (DWI).
Figure 5B:
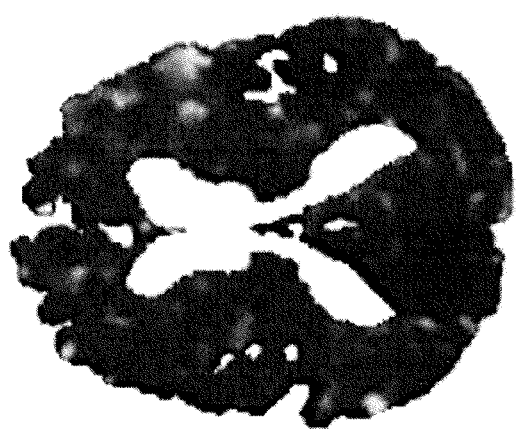
Figure 5A:
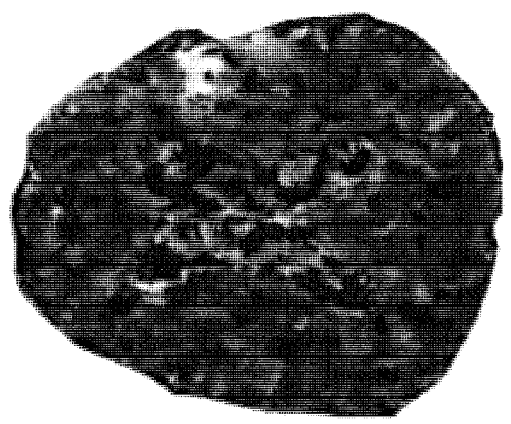

Referring now to FIGS. 5A-5C, shown therein are an example of pairs of perfusion functional maps determined for a second patient where the first column of images (FIG. 5A) are obtained using the CTP framework, the second column of images (FIG. 5B) are obtained using the TRH-CTA framework described in accordance with the teachings herein and the last column of images (FIG. 5C) are 24 hour diffusion weighted images (DWI). The second patient is an ischemic stroke patient with a small ischemic lesion from a left middle cerebral artery occlusion. At admission CT perfusion (CTP) "T0" functional perfusion imaging was performed and is shown in two slices (see FIG. 5A) and temporally resolved helical CTA (TRH-CTA) derived perfusion "Delay" maps were obtained (see FIG. 5B), while 24 hour diffusion weighted images (DWI) were also obtained (see FIG. 5C). The patient did not reperfuse (blood clot remained). The bright area on the DWI represents dead tissue (infarct) which correlates with the brighter values on the CTP and TRH-CTA functional images. Both the CTP and TRH-CTA correlates with final infarct volume.

Accordingly, the inventors have found that TRH-CTA image data can provide information on parenchymal hemodynamics distal to the occlusion, similar to CT perfusion (CTP). In fact, the inventors have discovered that the effectiveness of the TRH-CTA perfusion technique is generally within 5-10% of the accuracy of CTP when identifying penumbra. However, TRH-CTA is a less expensive and a more widely available modality while perfusion CT requires 8-30 minutes from image acquisition to interpretation and needs costly computational hardware and software for postprocessing images that are vendor specific, not standardized, and therefore variable across centers.

Furthermore, CTP has a number of drawbacks that TRH-CTA does not have. For example, with CTP it is more likely that patient motion can affect results since more image data needs to be acquired. CTP also additional radiation exposure to the patient and the need for additional contrast agents. CTp also has variations in technique with different vendor equipment and significant variability across vendors for the degree of coverage of the brain with CTP (e.g. 4 to 16 cm). Also some vendors have the option of covering 8 cm using a 'toggle table' technique that may introduce additional errors. Finally, there is still a lack of consensus in the medical community regarding the interpretation and best practices for treatments based on CTP perfusion maps.

Study #2

Patients

A post-hoc analysis was also performed using data from the Calgary Stroke Program's PRove-IT and ESCAPE studies (Goyal et al., 2015; Menon et al., 2015). AIS patients were included in the study if they presented within 12 hours from last seen normal. Inclusion criteria for the patient in the study were as follows: 1) patient age >18 years; 2) known symptom onset time; 3) any occlusion of the anterior circulation, which could be targeted for EVT; 4) patients had successful reperfusion assessed by digital subtraction angiography at the end of the EVT, and 5) patients had next day follow-up diffusion-weighted MR imaging (DWI) between 24-48 hours of admission. A modified Thrombolysis in Cerebral Infarction (mTICI) score of 2b or 3 was considered successful reperfusion (Saver et al, 2015; Campbell et al., 2015; Albers et al., 2018; Haussen et al., 2016; Nogueira et al., 2018a; Nogueira et al., 2018b; d'Esterre et al., 2015; Goyal et al., 2015; and Menon et al., 2015). Demographic and clinical characteristics, medical history, and any relevant workflow time intervals were collected prospectively. The study was approved by the local ethics board.

Image Acquisition

At admission, all patients had a standard non-contrast CT (NCCT) scan (5 mm slice thickness), a head/neck multi-phase CTA (i.e. TRH-CTA), and cine CT perfusion (CTP) with a craniocaudal coverage of 8 cm. The acquisition of raw image data for TRH-CTA imaging has been described previously (Menon et al., 2015). Briefly, 80 ml of an iodinated contrast agent was injected at a rate of 5 ml/sec followed by a saline flush of 50 ml at 6 ml/sec. For the first phase (7 seconds), the aortic arch-to-vertex helical scan was timed to be in the peak arterial phase by triggering the scan with contrast bolus tracking. The second phase was acquired after a delay of 4 seconds allowing the table to reposition to the skull base. Scan duration for the next 2 additional phases was 3.4 seconds. TRH-CTA acquisition data was reconstructed into axial image slices of 0.625 mm thickness. For the cine CTP protocol, 45 ml CT contrast agent (Optiray® 320; Mallinckrodt Pharmaceuticals; Dublin, Ireland) was power injected at 4.5 ml/s followed by a saline chase of 40 ml at 6 ml/s. Images for a section of 8 cm thickness were acquired at 5 mm slice thickness. Scanning began after a delay of 5 seconds from contrast injection for up to two phases (scanning intervals): $1^{st}$ phase every 2.8 s for 60 seconds and an additional $2^{nd}$ phase every 15 seconds for 90 seconds (total scan time=150 seconds).

Between 24-48 hours after treatment, a clinical DWI scan was acquired using a 3T MRI (Signa VH/i; GE Healthcare) flip angle 90° single-shot echo-planar sequence (b=0 s/mm$^{-2}$ and isotropic b=1000 s/mm$^{-2}$; repetition time=9000 ms; echo time=80-90 ms; 240 mm field-of-view; 5.0 mm slice thickness with a 0 or 2 mm gap).

Image Processing

The Perfusion Functional Map Processing: To generate functional images from the TRH-CTA image data, each phase of the mCTA was registered to the NCCT using a rigid registration. The NCCT was used to determine the baseline Hounsfield Unit for each region of the brain in a respective patient. The dynamic series generated from the NCCT and mCTA were post-processed with the following steps: i) the skull and ventricles were removed using per patient HU thresholds on the NCCT (ventricles=0-12 HU, Skull>60 HU). Time-attenuation curves (TAC) were created for each voxel after subtraction of the baseline NCCT HU values, which is a normalization technique that is common in perfusion processing (d'Esterre et al.; 2015).

Deconvolution (Fourier based) (Weiner, 1964) and non-deconvolution approaches were applied to the data from the time-attenuation density curves to generate the single metric hemodynamic functional maps (d'Esterre et al., 2015; Konstas et al., 2009). For the non-deconvolution approach, five hemodynamic functional maps were created: 1) time to peak (TTP)=the mCTA phase with the highest magnitude HU; 2) phase 1 blood flow=the slope of the first and second HU magnitude from the mCTA; 3) phase 2 blood flow=the slope of the second and third HU magnitude from the mCTA; 4) Flow average=the average of phase 1 blood flow and phase 2 blood flow; and 5) Blood volume=integral of the of TAC. For the deconvolution approach, a cerebral blood flow map was created. All of these functional maps can then be used inputs for a machine learning algorithm, to generate an optimized combination functional map.

A backwards step-wise logistic regression model was then trained using the remaining functional maps to create a combination functional map from the TRH-CTA image data. The logistic regression coefficients were varied inside of an exponential function to iteratively evaluate the discriminatory ability of the model to distinguish infarction and non-infarction at a voxel-level. The equation that was fit to the data is shown in equation (1):

$$P = \frac{1}{1+e^{-(A+BX+CY+DZ+EW)}} \quad (1)$$

where P is probability of a binomial outcome (between 0 and 1), A is a scaling constant, W, X, Y, Z are single metric functional maps, and B, C, D, E are the respective coefficients. Any combination of initial perfusion maps can be used, but these maps can also be first assessed to determine which are the best performing maps for detection and then the best performing maps can be provided to the logistic regression model, to obtain the coefficients and generate the optimized TRH-CTA-based perfusion map. Alternatively, other combinations of initial perfusion maps may be used, but there will be varying detection accuracies as well as depending on different characteristics of the stroke such as the type of stroke that occurs and the location where the stroke occurs.

In a sub-set of 40 patients, GE-CTP functional maps were processed by an expert using commercially available deconvolution software (CT Perfusion 4D, General Electric Healthcare, Waukesha, WI). For each study, the arterial input function (AIF) was manually selected from the basilar artery or contralateral ICA using a 2 voxel×2 voxel (in-slice) region-of-interest (ROI). The AIF is a function that results from measuring the Hounsfield units in each phase of TRH-CTA image data from the ICA or basilar arteries. It may be measured by recording the 3 data points in the ICA during each of the 3 phases of the TRH-CTA image data and then deconvolving those from the rest of the TRH-CTA image data. The optimal AIF, chosen from the basilar artery or ICA, will have the earliest contrast arrival time (i.e. when a signal is starting to be shown by a rise in Hounsfield Units) and have the highest magnitude (i.e. height of the TDC). The latter indicates that there's minimal partial volume averaging.

For all AIFs, baseline to peak height Hounsfield unit (HU) differences matched those from the respective sagittal sinus. Absolute maps of cerebral blood flow [CBF; ml·min$^{-1}$·(100 g)$^{-1}$], mean transit time (MTT; seconds), start time of the impulse residue function (i.e., delay of the tissue time-density curve with respect to the AIF) ($T_o$; s), and Tmax=$T_o$+0.5*MTT (s) were calculated by deconvolution of tissue time-density curves and the AIF using a delay-insensitive algorithm (CT Perfusion 4D, GE Healthcare). Average maps were created by averaging the serial (dynamic) CTP images over the duration of the first pass of contrast. These average maps have suitable anatomical detail for gray/white matter segmentation and as the source image for registration with follow-up imaging. In-plane patient motion was corrected in the x/y-axis using automated software (CT Perfusion 4D), and in cases with extreme motion, time points were manually removed as needed (Menon et al., 2015).

Perfusion map registration: All perfusion parameter maps generated from the mCTA and CT perfusion studies respectively were registered to the follow-up DWI dataset. Therefore, the optimal rigid transformation was computed between the follow-up DWI and average CTP or NCCT dataset, respectively, using the mutual-information image similarity metric within a multi-resolution approach (Studholme et al., 1196; Gobbi et al., 2003). The resulting transformations were then used to transform the perfusion maps to the follow-up DWI dataset using linear interpolation to validate the logistic regression model.

Infarct segmentation and perfusion data extraction: Delineation of the follow-up infarct volume (ROI-1) was performed on the follow-up DWI by applying a single standardized intensity (Sah et al., 2017). A non-infarct region of interest (ROI-2) encompassed any brain tissue outside of ROI-1, including voxels from the contralateral hemisphere. Subcortical structures (i.e. basal ganglia, including caudate, lentiform and internal capsule) were manually segmented and analyzed separately from cortical gray/white matter.

Histograms were generated for all ROI-1 and ROI-2 segmentations, respectively, from the TRH-CTA based-perfusion images as well as the CTP Tmax and CBF maps, as these maps have been previously shown by the inventors to have the highest accuracy for final infarction (d'Esterre et al., 2017). Patient-level histograms from ROI-1 and ROI-2 were amalgamated to create a single "all patient" ROI-1 and ROI-2 to perform a cohort-level analysis.

An additional analysis was undertaken to evaluate the effect of lesion size on the TRH-CTA-based lesion detection method described. Lesions at different size intervals were chosen, while larger or smaller lesions were eliminated from the analysis. This interval mean was shifted from 0.015 ml to 1000 ml, with the upper and lower bounds on the interval being 10% of the mean (i.e. 100 ml mean, 90-110 ml interval). This analysis was completed to determine if smaller petechial lesions were not identified by the TRH-CTA imaging protocol.

Statistical Analysis

Clinical data were summarized using standard descriptive statistics. A patient-level analysis and cohort-level analysis was performed using receiver operator characteristic curve analysis. At the patient level, the area under the ROC curve (AUC) was determined for each patient. At the cohort level, an AUC-ROC was determined for all infarct voxels and non-infarct voxels from all patients in an amalgamated histogram. Youden's method was used to determine optimal thresholds most associated with follow-up MRI infarct volume along with respective sensitivities and specificities for each threshold (Akobeng, 2007). AUC values were compared between the TRH-CTA-based and CTP-based cerebral blood flow and Tmax maps.

A cross validation for the TRH-CTA-based map (derived from the logistic regression model) was performed as it was the best performing map from the patient- and cohort-level analysis. The analysis was performed on the cohort-level histograms using a 10-fold cross validation to assess the performance and consistency of the TRH-CTA-based map. Each training set formed 90%, with replacement, of the total population and trained the ROC analysis to determine an optimal threshold. The optimal threshold was then applied to the remaining 10% of the total population to assess sensitivity, specificity, AUC, and optimal threshold. This process was completed 10 times to determine a mean and standard deviation in each of the above metrics.

A two sided p-value<0.05 was considered as statistically significant for all statistical tests. All analyses were performed using R (version 3.2.1), STATA (version13, Stata-Corp LP, College Station, TX) and MATLAB (R2015a, version 8.5, Mathworks Inc, Natick, MA) statistical packages.

Results

Of a total of n=80 patients satisfying study inclusion/exclusion criteria, n=72 were included in the study. Some patients (N=8) had inadequate registration results due to severe motion of one of the NCCT or mCTA series. Clinical demographics, including are summarized in Table 1. Median (IQR) DWI volume (ml) was 12 ml (with a range of 2.2-41.8 ml). The optimal TRH-CTA-based functional map derived from the logistic regression was generated from the deconvolution T0, and non-deconvolution TTP, CBF and MTT. This optimized TRH-CTA-based functional map was used in the patient and cohort level analysis as well the cross validation analysis.

TABLE 1

Admission demographics, site of occlusion and workflow metrics

| Variables | Total included patients, n = 72 |
|---|---|
| Age, y, median (minimum-maximum) | 68 (32-89) |
| Men, n (%) | 37 (51.4) |
| Stroke on awakening, n (%) | 27 (46.6) |
| Site of occlusion, n (%) | |
| MCA | 29 (40.3) |
| ACA | 3 (4.0) |
| ICA | 16 (22.2) |
| Tandem | 5 (6.9) |
| Affected hemisphere, n (%) | |
| Right | 30 (41.7) |
| Left | 39 (54.2) |
| Coronary Artery Disease, n (%) | 12 (16.7) |
| Congestive Heart Failure, n (%) | 6 (8.3) |
| Valvular Disease, n (%) | 2 (3.4) |
| Hypertension, n (%) | 38 (52.8) |
| Dyslipidemia, n (%) | 24 (33.3) |
| Diabetes, n (%) | 1 (1.4) |
| Smoking, n (%) | 20 (27.8) |
| Statin, n (%) | 22 (37.9) |
| EVT Treatment, n (%) | 72 (100) |
| tPA (alteplase) Treatment, n(%) | 55 (76) |
| Reperfusion CRF (TICI2B/3), n (%) | 72 (100) |
| Blood Glucose, mmol, median (minimum-maximum) | 6 (4.4-20.0) |
| NIHSS baseline, median (minimum-maximum) | 17 (1-29) |
| NIHSS 24-hours, median (minimum-maximum) | 6 (0-24) |
| MRS baseline, median (minimum-maximum) | 0 (0-3) |
| MRS 90-days, median (minimum-maximum) | 2 (0-6) |
| CT to Reperfusion Time, hh:mm, median (minimum-maximum) | 1:28 (0:27-3:06) |

Comparing ROC-AUC in patients with early and late reperfusion for cortical gray matter+white matter, there was no significant difference at the patient-level (0.83 vs. 0.84 respectively), the cohort-level (0.82 vs. 0.81 respectively) or the cross-validation (0.77 vs. 0.74 respectively) (see Table 2). Comparing ROC-AUC in patients with early and late reperfusion for basal ganglia tissue, there was no significant difference at the patient-level (0.82 vs. 0.84 respectively), the cohort-level (0.81 vs. 0.80 respectively) or the cross-validation (0.82 vs. 0.78 respectively) (see Table 3).

TABLE 2

Receiver operator characteristic curve AUC for TRH-CTA-based map, stratified by CT to reperfusion time for cortical gray + white matter tissue

| Statistic | AUC-Patient Level | AUC - Cohort Level | Cross validation Sensitivity | Cross Validation Specificity | Cross Validation Accuracy |
|---|---|---|---|---|---|
| TRH-CTA - Early Reperfusion, <90 mins (n = 49 patients) | | | | | |
| Mean | 0.83 | 0.82 | 0.82 | 0.72 | 0.77 |
| Stdev | 0.14 | N/A | 0.06 | 0.03 | 0.06 |
| TRH-CTA - Late Reperfusion, >90 mins (n = 24 patients) | | | | | |
| Mean | 0.84 | 0.81 | 0.79 | 0.70 | 0.74 |
| Stdev | 0.11 | N/A | 0.08 | 0.06 | 0.07 |

TABLE 3

Receiver operator characteristic curve AUC for TRH-CTA-based map, stratified by CT to reperfusion time for basal ganglia regions

| Statistic | AUC-Patient Level | AUC-Cohort Level | Cross Validation Sensitivity | Cross Validation Specificity | Cross Validation Accuracy |
|---|---|---|---|---|---|
| TRH-CTA - Early Reperfusion, >90 mins (21 patients) | | | | | |
| Mean | 0.82 | 0.81 | 0.82 | 0.81 | 0.82 |
| Stdev | 0.11 | N/A | 0.05 | 0.06 | 0.06 |
| TRH-CTA - Late Reperfusion, <90 mins (7 patients) | | | | | |
| Mean | 0.84 | 0.80 | 0.86 | 0.71 | 0.78 |
| Stdev | 0.1 | N/A | 0.08 | 0.09 | 0.09 |

In the patient-level ROC analysis, the SPIRAL map had a slightly higher, though non-significant (p<0.05) average ROC-AUC (cortical GM/white matter=0.82; Basal ganglia=0.79 respectively) than both the CTP-Tmax (cortical GM/white matter=0.82; Basal ganglia=0.78 respectively) and CTP-CBF (cortical GM/white matter=0.74; Basal ganglia=0.78 respectively) perfusion maps. The same relationship was observed at the cohort level (see Table 4).

TABLE 4

Receiver operator characteristic curve AUC for TRH-CTA-based map comparison with cine CTP maps for a 40 patient sub-cohort

| Statistic | Mean (stdev) Cortical GM + white matter | Mean (stdev) Basal ganglia |
|---|---|---|
| TRH-CTA-based Map | | |
| AUC-Patient Level | 0.83 (0.14) | 0.79 (0.08) |
| AUC-Cohort Level | 0.82 | 0.80 |
| CTP T-MAX Map | | |
| AUC-Patient Level | 0.82 (0.13) | 0.78 (0.11) |
| AUC-Cohort Level | 0.81 | 0.74 |
| CTP Blood Flow Map | | |
| AUC-Patient Level | 0.74 (0.14) | 0.78 (0.09) |
| AUC-Cohort Level | 0.72 | 0.77 |

Figure 6:
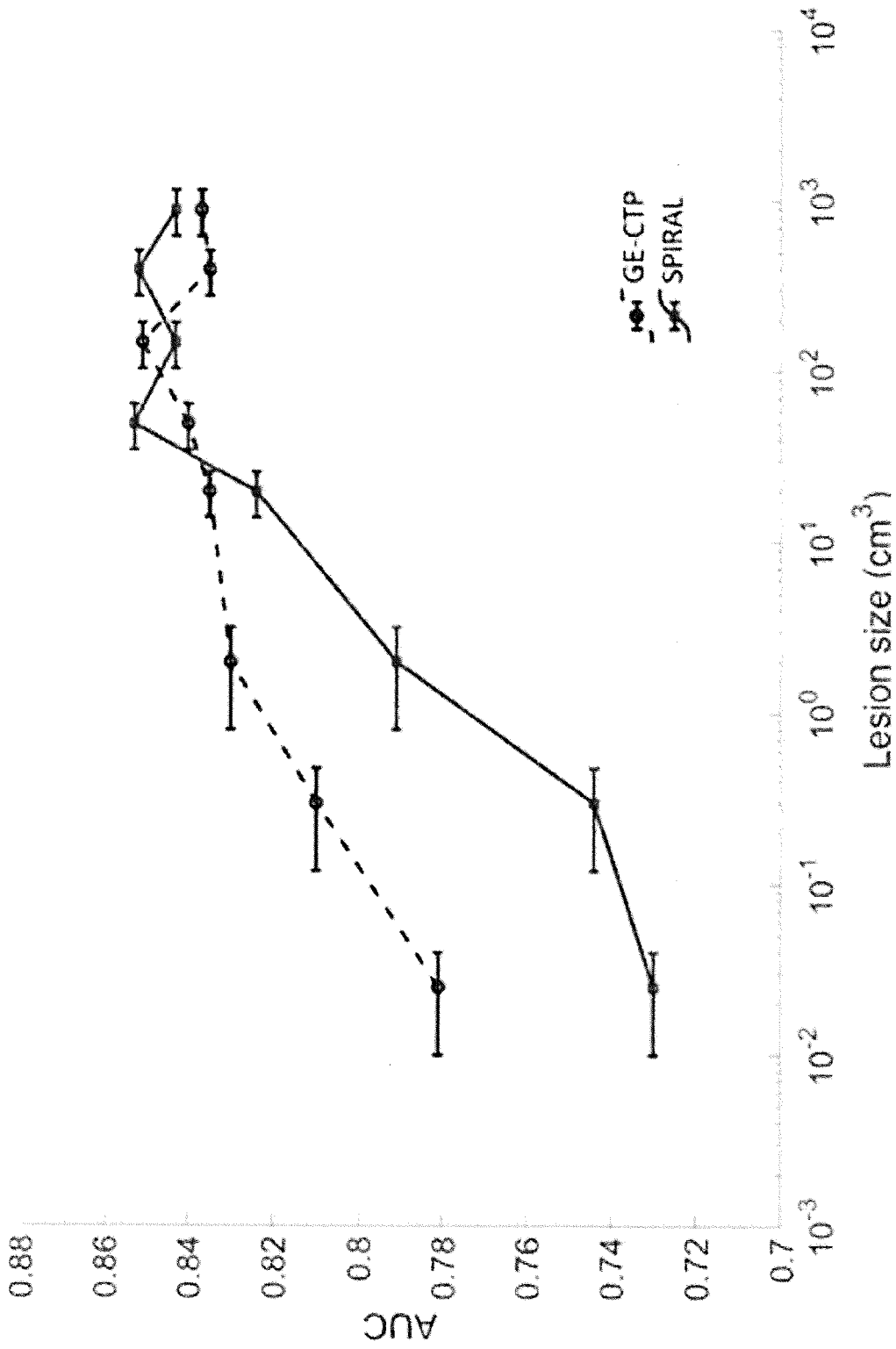
FIG. 6 shows a plot of sensitivity for final infarction on 24 hour MRI versus lesion size for TRH-CTA and CTP-Tmax maps.

The TRH-CTA-based map was significantly less accurate to detect smaller lesions (1-10 mL) while equally as accurate to identify larger lesions (>100 mL) compared to GE-CTP (see FIG. 6). This may be due to using less data points since the spatial resolution in the TRH-CTA image data is decreased in order to increase the signal-to-noise ratio by "smoothing" out noise. Therefore, if there are small lesions, those may be smoothed out. This might be improved by optimizing the filtering process.

Perfusion from low temporally sampled contrast enhanced imaging has been previously shown in a seminal paper by Heinz et al. 1979 (Reid et al, 2018). Similarly, it is shown herein that perfusion maps can be successfully generated from a temporally sampled helical CTA, potentially obviating the need for an additional cine CTP scan in the future. The accuracy, sensitivity, and specificity for follow-up infarct volume is similar to reported values from the CTP literature and the current CTP paradigm available at the inventors' institute (d'Esterre et al., 2013). The inventors have recently shown that perfusion measured on mCTA source images can better predict follow-up infarction and clinical outcomes when compared to NCCT and mCTA-rLMC (pial collateral scoring), the current paradigm used by the Calgary Stroke Program (Zerna et al., 2016; Shamy et al., 2013). Furthermore, NCCT and CTA collateral score for stroke decision making requires expert interpretation, contributing diagnostic uncertainty among non-experts (Shamy et al., 2013; Moeller et al., 2008).

Figures 7A, 7B, 7C:
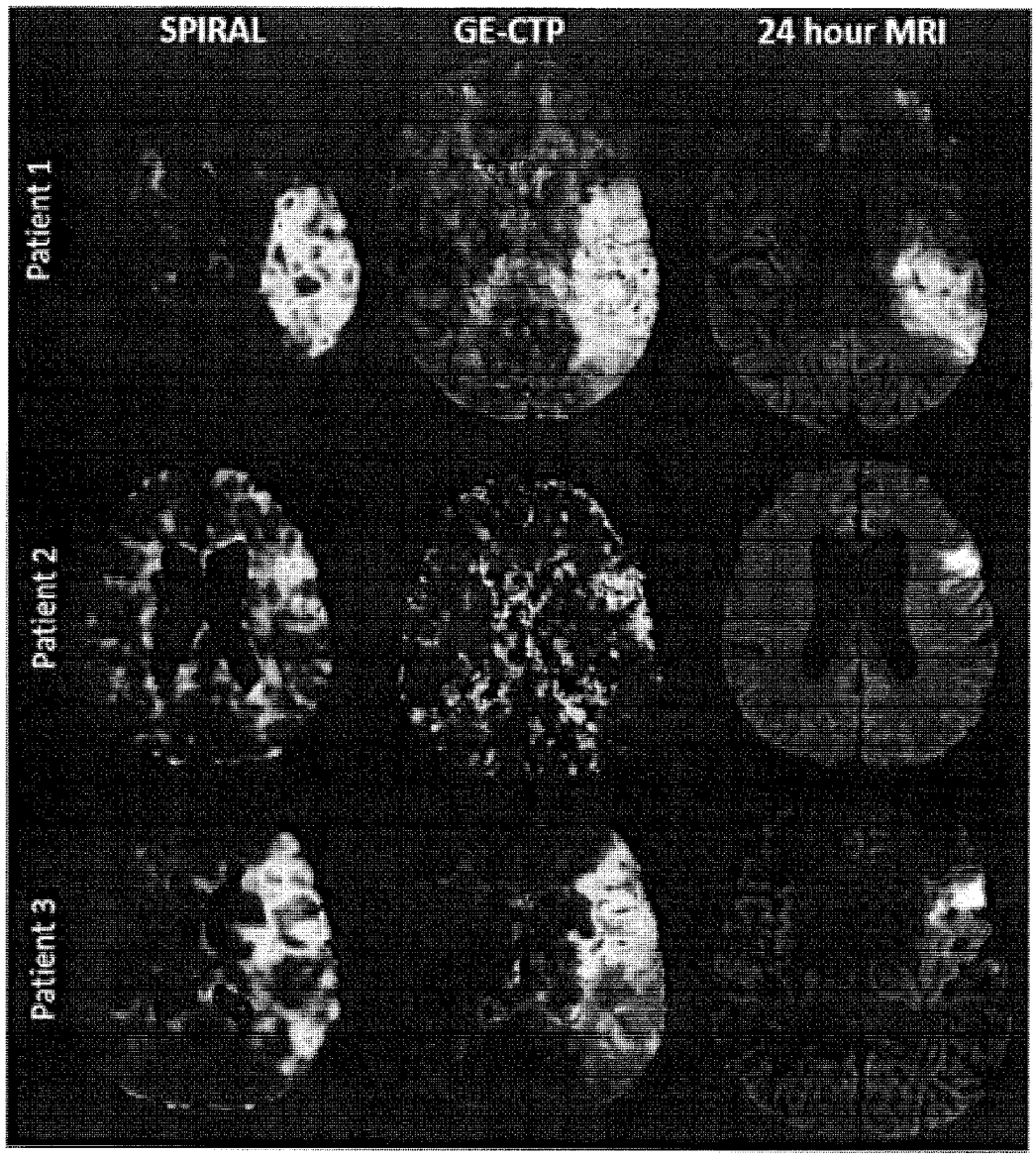
FIGS. 7A-7C show the admission TRH-CTA map, the CTP Tmax map and the 24 hour MR-DWI image for three patients respectively who underwent EVT for M1 occlusions and had quality/fast reperfusion with the final infarct volume being outlined on the 24 hour MR-DWI image.

Advantageously, the TRH-CTA imaging workflow of the present teachings provide an objective, easy to interpret, inexpensive, and time-sensitive imaging paradigm to characterize the ischemic lesion at admission with the TRH-CTA imaging protocol. For example, FIGS. 7A-7C provide three case study examples of images obtained with the TRH-CTA imaging protocol versus GE-CTP Tmax functional maps.

Improving patient outcome in acute stroke patients depends on fast treatment, high diagnostic accuracy, and confidence among non-expert physicians because stroke patient outcomes are heavily dependent on these factors. Brain imaging plays a key role in decision making that has required expert interpretation (Wintermark et al., 2013; Goyal et al., 2013; Sheth et al., 2012; Menon et al., 2014; Kudo et al., 2010; Bivard et al., 2013; Menon et al., 2015; Nambiar et al., 2014; Mishra et al., 2014), but among non-stroke experts it is a major cause for treatment delays (Shamy et al., 2013; Barber et al., 2001). CT angiography (CTA) is required to identify large vessel occlusion that may be amenable to remove via endovascular thrombectomy (EVT). Canadian guidelines strongly recommend use of CT Perfusion (CTP) to select acute ischemic stroke patients for EVT in the late time window at about 6-24 hours after symptom onset (Boulanger et al., 2018), and also has the advantage that it can improve diagnostic accuracy for the identification of ischemic stroke (Hoang et al., 2013). Although, CTP is a required modality for all Comprehensive Stroke Centres, CTP has significant limitations; CTP requires a separate image acquisition and post processing (delaying treatment), another contrast injection (increasing risk of acute nephropathy), and additional exposure to ionizing radiation (increased cancer risk). Finally, CTP has not been widely adopted in rural stroke centres (Menon et al., 2015; Davenport et al., 2013). However, the study results included herein, show that TRH-CTA-based functional maps can accurately identify infarct core, and is faster, less expensive, and likely safer technique for obtaining brain blood flow perfusion maps from a time resolved helical CT angiogram.

It should be noted that study #2 used highly selected patients with moderate to severe stroke symptoms that were treated with EVT and achieved very good and fast reperfusion to achieve an operational definition of "infarct core". Several patients were removed from study #2 due to the inability to register the images (motion correction to obtain the time attenuation curve. Nevertheless, the number of patients removed due to this error is consistent with other studies (d'Esterre et al., 2015). In study #2, the gray and white matter tissue compartments were not separated to determine respective accuracies—compared to CTP where an "Average Map" provides adequate gray/white differentiation, a low temporally resolved CTA cannot provide this.

As described herein, the TRH-CTA imaging protocol has the potential for reducing the time for image acquisition and radiological interpretation compared to NCCT, CTA collateral scores, and cine CT perfusion techniques. It is also believed that standardized TRH-CTA automation will maintain the diagnostic accuracy of cine CTP based paradigms, thus providing the potential for supporting significant improvements in stroke triaging, both in comprehensive and primary stroke centres. The TRH-CTA imaging protocol may also improve the generalizability of stroke reperfusion treatments outside the comprehensive tertiary care centres in both urban and rural communities. Other potential effects of the TRH-CTA imaging protocol are improved resource utilization and cost of imaging as TRH-CTA imaging does not require sophisticated processing or trained personnel beyond the acquisition of a dynamic helical CTA.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

Abels B, Klotz E, Tomandl B F, Kloska S P, Lell M M, (2010), "Perfusion CT in Acute Ischemic Stroke: A Qualitative and Quantitative Comparison of Deconvolution and Maximum Slope Approach", American Journal of Neuroradiology, October, 31(9): 1690-1698.

Akobeng A K. (2007), "Understanding diagnostic tests 3: Receiver operating characteristic curves", Acta Paediatr. 96:644-647.

Barber P A, Zhang J, Demchuk A M, Hill M D, Buchan A M, (2001), "Why are stroke patients excluded from tpa therapy? An analysis of patient eligibility", Neurology, 56:1015-1020.

Bivard A, Levi C, Spratt N, Parsons M., (2013), "Perfusion ct in acute stroke: A comprehensive analysis of infarct and penumbra", Radiology, 267:543-550.

Boulanger J M, Lindsay M P, Gubitz G, Smith E E, Stotts G, Foley N, et al., (2018), "Canadian stroke best practice recommendations for acute stroke management: Prehospital, emergency department, and acute inpatient stroke care, 6th edition, update 2018", International journal of stroke: official journal of the International Stroke Society, 13:949-984.

Davenport M S, Khalatbari S, Dillman J R, Cohan R H, Caoili E M, Ellis J H., (2013), "Contrast material-induced nephrotoxicity and intravenous low-osmolality iodinated contrast material", Radiology, 267:94-105.

d'Esterre C D, Boesen M E, Ahn S H, Pordeli P, Najm M, Minhas P, Davari P, Fainardi E, Rubiera M, Khaw A V, Zini A, Frayne R, Hill M D, Demchuk A M, Sajobi T T, Forkert N D, Goyal M, Lee T Y, Menon B K, (2015), "Time-Dependent Computed Tomographic Perfusion Thresholds for Patients With Acute Ischemic Stroke", Stroke, 46:3390-3397.

Fang R, Zhang S, Chen T, Sanelli P C, (2015), "Robust Low-dose CT Perfusion Deconvolution via Tensor Total-Variation Regularization" IEEE Trans. Med. Imaging, July; 34(7): 1533-1548.

Frölich A M, Wolff S L, Psychogios M N, et al. (2014), "Time-resolved assessment of collateral flow using 4D CT angiography in large-vessel occlusion stroke" Eur. Radiol.; 24(2), pp. 390-396.

Gobbi D G, Peters T M., (2003), "Generalized 3d nonlinear transformations for medical imaging: An object-oriented implementation in vtk", Comput Med Imaging Graph, 27:255-265.

Goyal M, Menon B K, Derdeyn C P., (2013), "Perfusion imaging in acute ischemic stroke: Let us improve the science before changing clinical practice", Radiology, 266:16-21.

Goyal M, Demchuk A M, Menon B K, Eesa M, Rempel J L, Thornton J, et al. (2015), "Randomized assessment of rapid endovascular treatment of ischemic stroke" New England Journal of Medicine. 372:1019-1030.

Hoang J K, Wang C, Frush D P, Enterline D S, Samei E, Toncheva G, et al., (2013), "Estimation of radiation exposure for brain perfusion ct: Standard protocol compared with deviations in protocol", American journal of roentgenology, 201:W730-734.

Horn J, Dankbaar J W, Schneider T., Cheng S C, Bredno J, Wintermark M, (2009), "Optimal Duration of Acquisition for Dynamic Perfusion CT Assessment of Blood-Brain Barrier Permeability Using the Patlak Model", American Journal of Neuroradiology, August, 30(7):1366-1370.

Konstas A A, Goldmakher G V, Lee T-Y, and Lev M H. (2009), "Theoretic basis and technical implementations of ct perfusion in acute ischemic stroke, part 2: Technical implementations", American Journal of Neuroradiology, 30:885-892.

Kudo K, Sasaki M, Yamada K, Momoshima S, Utsunomiya H, Shirato H, et al., (2010), "Differences in ct perfusion maps generated by different commercial software: Quantitative analysis by using identical source data of acute stroke patients", Radiology, 254:200-209.

Menon B K, O'Brien B, Bivard A, et al. (2013), "Assessment of leptomeningeal collaterals using dynamic CT angiography in patients with acute ischemic stroke", J. Cereb. Blood Flow Metab.; 33(3), pp. 365-371.

Menon B K, Almekhlafi M A, Pereira V M, Gralla J, Bonafe A, Davalos A, et al., (2014), "Optimal workflow and process-based performance measures for endovascular therapy in acute ischemic stroke: Analysis of the solitaire fr thrombectomy for acute revascularization study", Stroke, 45:2024-2029.

Menon B K, d'Esterre C D, Qazi E M, Almekhlafi M, Hahn L, Demchuk A M, and Goyal, M. (2015), "Multiphase CT Angiography: A New Tool for the Imaging Triage of Patients with Acute Ischemic Stroke", Radiology, Vol. 275, No. 2, May, pp. 510-520.

Mishra S M, Dykeman J, Sajobi T T, Trivedi A, Almekhlafi M, Sohn S I, et al., (2014), "Early reperfusion rates with iv tpa are determined by cta clot characteristics", Am J Neuroradiol, December; 35(12):2265-72.

Moeller J J, Kurniawan J Fau-Gubitz G J, Gubitz G j Fau-Ross J A, Ross Ja Fau-Bhan V, Bhan V., (2008), "Diagnostic accuracy of neurological problems in the emergency department", Can J. Neurol. Sci., July; 35(3): 335-41.

Nambiar V, Sohn S I, Almekhlafi M A, Chang H W, Mishra S, Qaz i E, et al., (2014), "Cta collateral status and response to recanalization in patients with acute ischemic stroke", American journal of neuroradiology, 35:884-890.

Reid M, Famuyide A O, Forkert N D, Sahand Talai A, Evans J W, Sitaram A, et al., (2018), "Accuracy and reliability of multiphase cta perfusion for identifying ischemic core", Clinical neuroradiology, September; 29(3):543-552.

Sah R G, d'Esterre C D, Hill M D, Hafeez M, Tariq S, Forkert N D, et al., (2017), "Diffusion-weighted mri stroke volume following recanalization treatment is threshold-dependent", Clinical neuroradiology, March; 29(1):135-141.

Shamy M C, Jaigobin C S., (2013), "The complexities of acute stroke decision-making: A survey of neurologists", Neurology, 81:1130-1133.

Sheth K N, Terry J B, Nogueira R G, Horev A, Nguyen T N, Fong A K, et al., (2012), "Advanced modality imaging evaluation in acute ischemic stroke may lead to delayed endovascular reperfusion therapy without improvement in clinical outcomes", *Journal of neurointerventional surgery.*, May; 5 Suppl. 1:i62-5

Studholme C, Hill D L, Hawkes D J., (1996), "Automated 3-d registration of mr and ct images of the head", *Med Image Anal.* 1:163-175.

Volny O, Cimflova P, Kadlecova P, Vanek P, Vanicek J, Menon B K, Mikulik R, (2017), "Single-Phase Versus Multiphase CT Angiography in Middle Cerebral Artery Clot Detection-Benefits for Less Experienced Radiologists and Neurologists", J Stroke Cerebrovasc Dis.; January; 26(1):19-24.

Weiner, N., (1964), Extrapolation, Interpolation and Smoothing of Stationary Time Series, Cambridge, Mass: MIT Press. ISBN 0-262-73005-7.

Wintermark M, Albers G W, Broderick J P, Demchuk A M, Fiebach J B, Fiehler J, et al., (2013), "Acute stroke imaging research roadmap ii", *Stroke,* 44:2628-2639.

Zerna C, Assis Z, d'Esterre C D, Menon B K, Goyal M., (2016), "Imaging, intervention, and workflow in acute ischemic stroke: The calgary approach", *American journal of neuroradiology,* 37:978-984.

The invention claimed is:

1. A system for providing at least one Computed Tomography Angiography (CTA) perfusion functional map, wherein the system comprises:
    at least one processor that is configured to:
        obtain Time Resolved Helical CTA (TRH-CTA) image data;
        preprocess the TRH-CTA helical image data to generate preprocessed TRH-CTA helical image data;
        generate time density curve data for a plurality of voxels from the preprocessed TRH-CTA helical image data for an axial imaging slice, where the time density curve data comprise intensity values for different phases of the preprocessed TRH-CTA helical image data arranged sequentially in time;
        generate the at least one perfusion functional map for the axial imaging slice by at least one of: (1) applying at least one mapping function to different phases of the time density curve data corresponding to the axial imaging slice; (2) applying a deconvolution method to the time density curve data; and (3) applying a non-deconvolution method to the time density curve data; and
        perform filtering in the spatial domain or the frequency domain on the at least one perfusion functional map; and
    a display that is coupled to the at least one processor for receiving and displaying the at least one filtered perfusion functional map.

2. The system of claim 1, wherein the at least one processor is configured to preprocess the TRH-CTA image data by:
    generating raw TRH-CTA image by performing reconstruction on the TRH-CTA image data;
    separating the raw TRH-CTA image data into separate groups of TRH-CTA time series data where each group corresponds to a distinct phase of the TRH-CTA image data; and
    performing registration on the separate groups of TRH-CTA time series data to align the separate groups of TRH-CTA time series data in 3D space.

3. The system of claim 2, wherein the at least one processor is further configured to generate the preprocessed TRH-CTA helical image data by:
    applying a first threshold to the groups of TRH-CTA time series data to remove or reduce contributions from a skull of the patient to values of the time series data points; and
    applying a second threshold to the groups of TRH-CTA time series data to remove or reduce contributions from cerebrospinal fluid of the patient to values of the time series data points.

4. The system of claim 1, wherein the at least one processor is configured to apply the mapping function to create:
    a delay map for a plurality of pixels corresponding to the axial imaging slice by, for a given pixel, selecting a highest intensity value of the time density curve data for the voxel that corresponds to the given pixel;
    a first blood flow map for a plurality of pixels corresponding to the axial imaging slice by, for a given pixel, determining a slope of the intensity value of the time density curve data over first and second phases of the voxel that corresponds to the given pixel;
    a second blood flow map for a plurality of pixels corresponding to the axial imaging slice by, for a given pixel, determining a slope of the intensity value of the time density curve data over second and third phases of the voxel that corresponds to the given pixel;
    a flow average perfusion functional map by averaging the first and second blood flow maps;
    a blood volume map for a plurality of pixels corresponding to the axial imaging slice by, for a given pixel, performing an integral of the time density curve data of the voxel that corresponds to the given pixel; and/or
    a washout map for a plurality of pixels corresponding to the axial imaging slice by, for a given pixel, subtracting an intensity value of a third phase from a highest intensity value of all phases of the time density data for the voxel that corresponds to the given pixel.

5. The system of claim 1, wherein the at least one processor is configured to apply the deconvolution method to the time density curve data corresponding to the axial imaging slice by using an arterial input function and preferably the deconvolution method is implemented based on one of a Fourier transform based deconvolution, standard truncated singular value decomposition (sSVD), block-circulant truncated SVD (bSVD), Tikhonov regularization and sparse perfusion deconvolution (SPD).

6. The system of claim 1, wherein the at least one processor is configured to apply the non-deconvolution to the time density curve data by applying a function that doesn't involve deconvolution including one of multiplication, subtraction, division, max slope approach, and the Patlak model.

7. The system of claim 1, wherein the at least one processor is configured to apply the mapping function to create a combination map for a plurality of pixels corresponding to the axial imaging slice by, for a given pixel, generating at least two functional maps and then combining the at least two functional maps by: (a) optionally applying coefficients to the at least two functional maps followed by applying a linear or non-linear function to combine the at least two functional maps or (b) by applying a machine learning model to the at least two functional maps and preferably the machine learning model comprises one of a decision tree, a support vector machine, principle component analysis, a random forest, and a neural network.

8. The system of claim 1, wherein the at least one processor is further configured to apply filtering to the at least one perfusion functional map by applying at least one of: (a) spatial filtering including moving average filtering, 3D Gaussian filtering, bilateral Gaussian filtering followed by a full Gaussian blur, or guided filtering; (b) spectral filtering including bandpass, low pass, high pass or band stop filtering in the frequency domain; or (c) iterative spatial and/or frequency filtering.

9. The system of claim 1, wherein the at least one processor is further configured to apply at least one threshold to the at least one perfusion functional map to generate an infarct and/or penumbra output volume for the axial imaging slice and display the infarct and/or penumbra output volume and optionally the at least one processor is further configured to apply additional filtering after the thresholding to remove small objects including small infarcts that are noise.

10. A method for providing at least one Computed Tomography Angiography (CTA) perfusion functional map, wherein the method is performed by at one processor and the method comprises:
    obtaining Time Resolved Helical CTA (TRH-CTA) image data;
    preprocessing the TRH-CTA helical image data to generate preprocessed TRH-CTA helical image data;
    generating time density curve data for a plurality of voxels for an axial imaging slice from the preprocessed TRH-CTA helical image data, where the time density curve data comprise intensity values for different phases of the preprocessed TRH-CTA helical image data arranged sequentially in time;
    generating the at least one perfusion functional map for the axial imaging slice by at least one of: (1) applying at least one mapping function to different phases of the time density curve data corresponding to the axial imaging slice; (2) applying a deconvolution method to the time density curve data; and (3) applying a non-deconvolution method to the time density curve data;
    perform filtering in the spatial domain or the frequency domain on the at least one perfusion functional map; and
    outputting, via a display, the at least one filtered perfusion functional map.

11. The method of claim 10, wherein the method comprises preprocessing the TRH-CTA image data by:
    generating raw TRH-CTA image by performing reconstruction on the TRH-CTA image data;
    separating the raw TRH-CTA image data into separate groups of TRH-CTA time series data where each group corresponds to a distinct phase of the TRH-CTA image data; and
    performing registration on the separate groups of TRH-CTA time series data to align the separate groups of TRH-CTA time series data in 3D space.

12. The method of claim 11, wherein the method further comprises generating the preprocessed TRH-CTA helical image data by:
    applying a first threshold to the groups of TRH-CTA time series data to remove or reduce contributions from a skull of the patient to values of the time series data points; and
    applying a second threshold to the groups of TRH-CTA time series data to remove or reduce contributions from cerebrospinal fluid of the patient to values of the time series data points.

13. The method of claim 10, wherein the method comprises applying the mapping function to create:
    a delay map for a plurality of pixels corresponding to the axial imaging slice by, for a given pixel, selecting a highest intensity value of the time density curve data for the voxel that corresponds to the given pixel;
    a first blood flow map for a plurality of pixels corresponding to the axial imaging slice by, for a given pixel, determining a slope of the intensity value of the time density curve data over first and second phases of the voxel that corresponds to the given pixel;
    a second blood flow map for a plurality of pixels corresponding to the axial imaging slice by, for a given pixel, determining a slope of the intensity value of the time density curve data over second and third phases of the voxel that corresponds to the given pixel;
    a flow average perfusion functional map by averaging the first and second blood flow maps;
    a blood volume map for a plurality of pixels corresponding to the axial imaging slice by, for a given pixel, performing an integral of the time density curve data of the voxel that corresponds to the given pixel; and/or
    a washout map for a plurality of pixels corresponding to the axial imaging slice by, for a given pixel, subtracting an intensity value of a third phase from a highest intensity value of all phases of the time density data for the voxel that corresponds to the given pixel.

14. The method of claim 10, wherein the method comprises applying deconvolution to the time density curve data corresponding to the axial imaging slice by using an arterial input function and preferably the method comprises performing deconvolution based on one of a Fourier transform based deconvolution, standard truncated singular value decomposition (sSVD), block-circulant truncated SVD (bSVD), Tikhonov regularization and sparse perfusion deconvolution (SPD).

15. The method of claim 10, wherein the method comprises applying the non-deconvolution to the time density curve data by applying a function that doesn't involve deconvolution including one of multiplication, subtraction, division, max slope approach, and the Patlak model.

16. The method of claim 10, wherein the method comprises applying the mapping function to create a combination map for a plurality of pixels corresponding to the axial imaging slice by, for a given pixel, generating at least two functional maps and then combining the at least two functional maps by: (a) optionally applying coefficients to the at least two functional maps followed by applying a linear or non-linear function to combine the at least two functional maps or (b) by applying a machine learning model to the at least two functional maps and preferably the method comprises implementing the machine learning model by using one of a decision tree, a support vector machine, principle component analysis, a random forest, and a neural network.

17. The method of claim 10, wherein the method comprises applying filtering to the at least one perfusion functional map by applying at least one of: (a) spatial filtering including moving average filtering, 3D Gaussian filtering, bilateral Gaussian filtering followed by a full Gaussian blur, or guided filtering; (b) spectral filtering including bandpass, low pass, high pass or band stop filtering in the frequency domain; or (c) iterative spatial and/or frequency filtering.

18. The method of claim 10, wherein the method comprises applying at least one threshold to the at least one perfusion functional map to generate an infarct and/or penumbra output volume for the axial imaging slice and display the infarct and/or penumbra output volume and optionally the method further comprises applying additional filtering after the thresholding to remove small objects including small infarcts that are noise.

19. A method for providing images used to determine a treatment method for treating a stroke patient, wherein the method comprises:
   administering a bolus of image contrast agent to the patient; and
   generating and displaying at least one TRH-CTA perfusion functional map according to the method defined in claim 10.

20. A non-transitory computer readable medium with program instructions stored thereon that, when executed by at least one processor, cause the at least processor to perform a method for providing at least one Computed Tomography Angiography (CTA) perfusion functional map, wherein the method comprises:
   obtaining Time Resolved Helical CTA (TRH-CTA) image data;
   preprocessing the TRH-CTA helical image data to generate preprocessed TRH-CTA helical image data;
   generating time density curve data for a plurality of voxels for an axial imaging slice from the preprocessed TRH-CTA helical image data, where the time density curve data comprise intensity values for different phases of the preprocessed TRH-CTA helical image data arranged sequentially in time;
   generating the at least one perfusion functional map for the axial imaging slice by at least one of: (1) applying at least one mapping function to different phases of the time density curve data corresponding to the at least one axial imaging slice; (2) applying a deconvolution method to the time density curve data; and (3) applying a non-deconvolution method to the time density curve data;
   performing filtering in the spatial domain or the frequency domain on the at least one perfusion functional map; and
   outputting, via a display, the at least one filtered perfusion functional map.

* * * * *